United States Patent
Gros et al.

(10) Patent No.: US 11,529,332 B2
(45) Date of Patent: *Dec. 20, 2022

(54) CORROLES FOR TREATING POXVIRUS INFECTION

(71) Applicants: UNIVERSITE DE BOURGOGNE, Dijon (FR); NéoVirTech SAS, Toulouse (FR)

(72) Inventors: Claude Gros, Neuilly les Dijon (FR); Franck Gallardo, Montauban (FR); Nicolas Desbois, Bessey les Citeaux (FR)

(73) Assignees: UNIVERSITE DE BOURGOGNE, Dijon (FR); NÉOVIRTECH SAS, Toulouse (FR)

( * ) Notice: Subject to any disclaimer, the term of this patent is extended or adjusted under 35 U.S.C. 154(b) by 300 days.

This patent is subject to a terminal disclaimer.

(21) Appl. No.: 16/767,693

(22) PCT Filed: Nov. 27, 2018

(86) PCT No.: PCT/EP2018/082720
§ 371 (c)(1),
(2) Date: May 28, 2020

(87) PCT Pub. No.: WO2019/105940
PCT Pub. Date: Jun. 6, 2019

(65) Prior Publication Data
US 2021/0169853 A1    Jun. 10, 2021

(30) Foreign Application Priority Data
Nov. 29, 2017    (EP) .................................... 17306656

(51) Int. Cl.
| A61K 31/409 | (2006.01) |
| A61P 31/20 | (2006.01) |
| A61K 31/4439 | (2006.01) |
| A61K 31/444 | (2006.01) |
| A61K 39/275 | (2006.01) |
| A61K 47/54 | (2017.01) |

(52) U.S. Cl.
CPC .......... *A61K 31/409* (2013.01); *A61K 31/444* (2013.01); *A61K 31/4439* (2013.01); *A61K 39/275* (2013.01); *A61K 47/546* (2017.08); *A61P 31/20* (2018.01)

(58) Field of Classification Search
CPC ............. A61K 31/409; A61K 31/4439; A61K 31/444; A61K 39/275; A61P 31/20
See application file for complete search history.

(56) References Cited

U.S. PATENT DOCUMENTS

| 8,791,099 B2 | 7/2014 | Gross et al. |
| 2011/0098262 A1* | 4/2011 | Yondim ............... C07D 487/22 548/402 |
| 2014/0045809 A1 | 2/2014 | Yondim et al. |

FOREIGN PATENT DOCUMENTS

| WO | 2009/027965 A1 | 3/2009 |
| WO | 2009/076449 A1 | 6/2009 |
| WO | 2009/095923 A2 | 8/2009 |

OTHER PUBLICATIONS

Paolesse et al., "Synthesis and Functionalization of meso-Aryl-Substituted Corroles", The Journal of Organic Chemistry, 2001, pp. 550-556, vol. 66, No. 2.
Gryko et al., "Refinded methods for the synthesis of meso-substituted A3- and trans-A2B-corroles", Organic & Biomolecular Chemistry, 2003, vol. 1, pp. 350-357, XP002595975.
International Search Report, dated Mar. 14, 2019, from corresponding PCT application No. PCT/EP2018/082720.
Gros et al., "Synthesis and Antiviral Activity Evaluation of Nitroporphyrins and Nitrocorroles as Potential Agents against Human Cytomegalovirus Infection", ACS Infectious Diseases, 2015, pp. 350-356, vol. 1, No. 8, XP009504313.
Kadish et al., "Clarification of the Oxidation State of Cobalt Corroles in Heterogeneous and Homogeneous Catalytic Reduction of Dioxygen", Inorganic Chemistry, 2008, pp. 6726-6737, vol. 47, XP055461939.
Carvalho et al., "Antimicrobial photodynamic activity of porphyrin derivatives: potential application on medical and water disinfection", Journal of Porphyrins and Phthalocyanines, 2009, pp. 574-577, vol. 13, XP055461677.

* cited by examiner

*Primary Examiner* — Timothy R Rozof
(74) *Attorney, Agent, or Firm* — Nixon & Vanderhye

(57) ABSTRACT

Disclosed is a family of corroles for their use in the treatment of an infection by poxvirus.

15 Claims, 2 Drawing Sheets

CORROLES FOR TREATING POXVIRUS INFECTION

BACKGROUND OF THE INVENTION

Field of the Invention

The present invention is related to a family of corroles for their use in the treatment of an infection by a poxvirus.

Description of the Related Art

Poxviruses are large dsDNA viruses infecting a broad variety of organisms from animal to human and divided into two groups: Chordopoxvirinae and Entomopoxvirinae. Poxviruses are pathogens responsible for many veterinary diseases. For example, Myxoma virus (MYXV) is the causing agent of myxomatosis in rabbits. Till now, the only efficient method to prevent this disease in rabbits is vaccination. However, the efficiency of vaccination lasts only between 6 months and a year. For MYXV, vaccination will not prevent infection in some cases, but symptoms will be attenuated.

Some poxvirus can also induce severe pathological infection in human. One example is smallpox, a deadly human disease globally eradicated in 1980 after vaccination campaigns throughout the 19$^{th}$ and 20$^{th}$ centuries. The pathogen of smallpox is variola virus (VARV), one member of the poxvirus family. There is no specific treatment for this disease. Vaccination, based on injection of Vaccinia virus (VACV) that confer a cross protection against VARV, is the only preventive method to prevent this disease. Considering bioterrorism threat and the risk of accidental or intentional resurgence of this virus, it is necessary to develop an efficient curative anti-poxviruses medicament to secure the use of VACV vaccine and oncolytic poxviruses and to broad distribution in case of bioterrorism threat. Current therapies are still in clinical phases, albeit stock of anti VACV ig can be mobilized in case of resurgence of VARV. Still today, small compounds inhibiting poxvirus infection has not been discovered.

SUMMARY OF THE INVENTION

Against all expectations, the Inventors of the present invention have observed that a family of corroles have efficient anti-infective activities on myxoma virus (MYXV) and their anti-infective activities on other virus of the family Poxviridae are also predictable.

The first subject matter of the present invention is to provide a corrole of type A3 or A2B of formula (I):

(I)

wherein:
$Y_1$ and $Y_2$ are identical or different and each independently chosen from, —H, —SO$_3$H, —SO$_3^-$, —NO$_2$, —CHO, —NH$_2$, —NH$_3^+$, —COOH, —COO$^-$ M represents 3H or a metal chosen from the group of Cu, Mn, Fe, Co, V, Cr, Ti, Ag, Rh, Ru, Mo, Zr, Au, Pt, Ir, Re, W, Hf, Li, Al, Ga, Ge, Sn, As, Sb, Pb, Bi, La, Gd, Tb, or Th $A_1$ and $A_2$ are identical or different and each represents a phenyl group of formula (II), (II)

or
a pyridinium group of formula (III)

(III)

or
a five membered heterocycle of formula (IV)

(IV)

with each of $R_1$, $R_2$, $R_3$, $R_4$ and $R_5$ of formula (II); each of $R_1'$, $R_2'$, $R_4'$ and $R_5'$ of formula (III); each of $R_1''$, $R_2''$, and $R_3''$ of formula (IV) being chosen from:
(a). —H, —CN, —NO$_2$, —CHO, —SO$_3$H, —OH, —SH, —C≡CH, —NH$_2$, —COOH, —CONH$_2$,
(b). a halogen atom, selected from a chlorine atom, a fluorine atom, a bromine atom, or an iodine atom,
(c). a (C$_1$-C$_8$) alkyl chain,
(d). a PEG chain of formula —(CH$_2$—CH$_2$—O)$_n$—H or of formula —(CH$_2$—CH$_2$—O)$_n$—CH$_3$, wherein n is an integer chosen from 1, 2, 3, 4 or 5,
(e). —CX$_3$, X being a halogen atom selected from a chlorine atom, a fluorine atom, a bromine atom, or an iodine atom,
(f). —OR$_a$, —NR$_a$R$_b$, —NHR$_a$, —COOR$_a$, —CONHR$_a$, —CONR$_a$R$_b$, —SO$_3$R$_a$, —SO$_2$NHR$_a$, —COR$_a$, —SR$_a$, —C≡CR$_a$, R$_a$ and R$_b$ being independently chosen from —(CH$_2$—CH$_2$—SO$_3$H), a (C$_1$-C$_8$) alkyl chain, a PEG chain of formula —(CH$_2$—CH$_2$—O)$_n$—H, or of formula —(CH$_2$—CH$_2$—O)$_n$—CH$_3$, wherein n is an integer chosen from 1, 2, 3, 4 or 5

(g). a group of formula $$-\!\!\!-\!\!\overset{O}{\underset{H}{\overset{\|}{C}}}\!\!-\!\!\underset{H}{N}\!\!-\!\!\underset{H_2}{C}\!\!-\!\!HC\!\!\overset{Rc}{\underset{SO_3H,}{\diagdown}}$$

wherein $R_c$ is —COOH, or —SO$_3$H,
(h). a pyridinium group of formula

[pyridinium structure with Rd on N+]

wherein $R_d$ is a (C$_1$-C$_8$) alkyl chain, or —(CH$_2$)$_n$SO$_3^-$, n being an integer chosen from 1, 2, 3, 4 or 5,
$R_3'$ of formula (III) being chosen from
—H, —CONH$_2$,
a (C$_1$-C$_8$) alkyl chain
a PEG chain of formula —(CH$_2$—CH$_2$—O)$_n$—H or of formula —(CH$_2$—CH$_2$—O)$_n$—CH$_3$, wherein n is an integer chosen from 1, 2, 3, 4 or 5,
a group —(CH$_2$)$_n$SO$_3^-$, n being an integer chosen from 1, 2, 3, 4 or 5
—OR$_a$, —NR$_a$R$_b$, —NHR$_a$, —COOR$_a$, —CONHR$_a$, —CONR$_a$R$_b$, —COR$_a$, R$_a$ and R$_b$ being independently chosen from —(CH$_2$—CH$_2$—SO$_3$H), a (C$_1$-C$_8$) alkyl chain, a PEG chain of formula —(CH$_2$—CH$_2$—O)$_n$—H, or of formula —(CH$_2$—CH$_2$—O)$_n$—CH$_3$ wherein n is an integer chosen from 1, 2, 3, 4 or 5,
E of formula (IV) is chosen from —O—, —S—, —Se—, —NH—,
or a pharmaceutically acceptable salt thereof, or an optical isomer thereof, for its use in the treatment of an infection of a poxvirus in human or non-human animals.

The corroles of the present invention are organic molecules having a contracted porphyrin ring comprising nineteen carbon atoms and 4 nitrogen atoms, and are capable of binding metals chosen from the group of Cu, Mn, Fe, Co, V, Cr, Ti, Ag, Rh, Ru, Mo, Zr, Au, Pt, Ir, Re, W, Hf, Li, Al, Ga, Ge, Sn, As, Sb, Pb, Bi, La, Gd, Tb, or Th.

According to the invention, the term "a corrole of type A3" is meant to be a corrole wherein the A$_1$ and the A$_2$ are identical. In another word, a corrole of type A3 is a corrole wherein the three substituent groups on meso position 5, 10 and 15 of said corrole are identical.

According to the invention, the term "a corrole of type A2B" is meant to be a corrole wherein the A$_2$ is different from the A$_1$. In another word, a corrole of type A2B is a corrole wherein the substituent groups on meso position 5 and 15 are identical and they are different from the substituent group on meso position 10 of said corrole.

The term "a (C$_1$-C$_8$)alkyl chain" is meant to a saturated straight or branched hydrocarbon chain containing from 1 to 8 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl.

The term "pharmaceutically acceptable salt" refers to those salts which are, within the scope of sound medical judgment, suitable for use in contact with the tissues of humans without undue toxicity, irritation, allergic response and the like.

A pharmaceutically acceptable salt of a corrole of formula (I) of the present invention refers to salts which retain the biological effectiveness of corrole of formula (I) and are not biological undesirable for human.

According to the present invention, a pharmaceutically acceptable salt of a compound of the invention can be a pharmaceutically acceptable, organic or inorganic acid or base salt of a compound of the invention.

A pharmaceutically acceptable salt of a corrole of formula (I) can be obtained by reacting said corrole with a variety of organic and inorganic positive counter ions well known in the art, for example sodium, potassium, calcium, magnesium, ammonium, tetraalkylammonium, and the like. A pharmaceutically acceptable salt of a corrole of formula (I) can also be obtained by reacting said corrole with pharmaceutically acceptable acids. Specific examples include inorganic acid salts such as hydrochlorides and sulfates; and organic acid salts such as formates, trifluoroacetates, acetates, tartrates, maleates, fumarates, succinates and methanesulfonates.

The term "optical isomers" refers to molecules that differ three-dimensionally by the placement of substituents around one or more atoms in a molecule.

According to an embodiment of corroles of type A2B of the present invention, A$_1$ and A$_2$ are both phenyl groups of formula II which are substituted differently.

In another embodiment of corroles of type A2B of the present invention, A$_1$ and A$_2$ are both pyridinium groups of formula II which are substituted differently.

In an embodiment of the corrole of the present invention, when A$_1$, A$_2$ or R$_3'$ is a pyridinium group which does not bear a —SO$_3$ group, said corrole comprises a counter ion such as Cl$^-$, Br$^-$ or I$^-$.

The term "poxvirus" is meant to be a virus of the family Poxviridae.

The corroles of the present invention are used for treating an infection in human or non-human animals by a poxvirus belonging to the subfamily Chordopoxvirinae or Entomopoxvirinae.

Examples of a virus of subfamily Chordopoxvirinae can be orthopoxvirus, parapoxvirus, capripoxvirus, leporipoxvirus, avipoxvirus, suipoxvirus, molluscipoxvirus, yatapoxvirus, crocodylidpoxvirus, or cervidpoxvirus.

Examples of a virus of subfamily Entomopoxvirinae are entomopoxvirus A, B or C.

According to the present invention, the non-human animals are especially chosen from cattle, sheep, goat, monkeys, baboons, rabbits, lagomorphs, squirrels, swine, deer, and birds.

In a particular embodiment, the corroles of the present invention are used for treating an infection of a poxvirus that is chosen from myxomatosis, cowpox, smallpox, sheeppox, orf, vaccinia, monkeypox, LSDV, goatpox or an infection by any other members of the poxvirus family In an embodiment of the corroles of formula (I), M represents 3H. Said corroles are represented by formula (Ia)

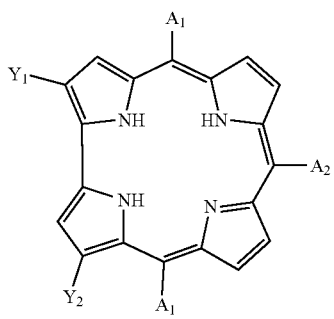
(Ia)

Wherein $Y_1$, $Y_2$, $A_1$ and $A_2$ are defined as in formula (I).

According to a more particular embodiment of the corroles of the present invention, $A_1$ and/or $A_2$ are represented by one formula chosen from the formula (IIa), (IIb), (IIc), (IId), (IIIa), (IIIb), (IIIc) or (IIId).

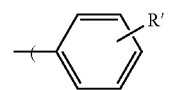
(IIa)

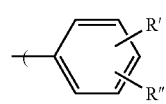
(IIb)

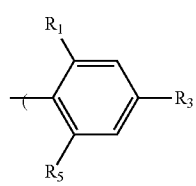
(IIc)

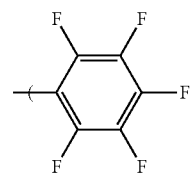
(IId)

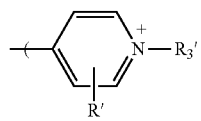
(IIIa)

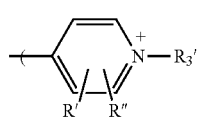
(IIIb)

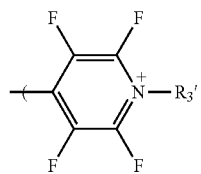
(IIIc)

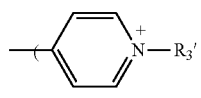
(IIId)

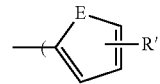
(IVa)

wherein R', R", $R_1$, $R_3$ and $R_5$ are independently chosen from:
- —CN, —NO$_2$, —CHO, —SO$_3$H, —OH, —NH$_2$, —COOH, —CONH$_2$, —SH, —C≡CH,
- a halogen atom, selected from a chlorine atom, a fluorine atom, a bromine atom, or an iodine atom,
- a (C$_1$-C$_8$)alkyl chain,
- a PEG chain of formula —(CH$_2$—CH$_2$—O)$_n$—H or of formula —(CH$_2$—CH$_2$—O)$_n$—CH$_3$, wherein n is an integer chosen from 1, 2, 3, 4 or 5,
- —CX$_3$, X being a halogen selected from a chlorine atom, a fluorine atom, a bromine atom, or an iodine atom,
- —OR$_a$, —NR$_a$R$_b$, —COOR$_a$, —NHR$_a$, —CONR$_a$R$_b$, —CONHR$_a$, —SO$_3$R$_a$, —SO$_2$NHR$_a$, —COR$_a$, —SR$_a$, —C≡CR$_a$, R$_a$ and R$_b$ being independently chosen from —(CH$_2$—CH$_2$—SO$_3$H), a (C$_1$-C$_8$)alkyl, a PEG chain of formula —(CH$_2$—CH$_2$—O)$_n$—H or of formula —(CH$_2$—CH$_2$—O)$_n$—CH$_3$, wherein n is an integer chosen from 1, 2, 3, 4 or 5,
- a group of formula

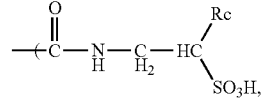

wherein R$_c$ is —COOH, or —SO$_3$H,
a pyridinium group of formula

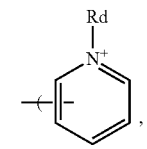

wherein R$_d$ is a (C$_1$-C$_8$) alkyl chain, or —(CH$_2$)$_n$SO$_3^-$, n being an integer chosen from 1, 2, 3, 4 or 5;
R$_3$' is as defined before.

Thus in this embodiment at least one of $A_1$ and $A_2$ or both of them are selected from (IIa), (IIb), (IIc), (IId), (IIIa), (IIIb), (IIIc), (IIId) or (IVa). $A_1$ and $A_2$ may be identical or different.

According to formula (IIa), R' represents any one of $R_1$, $R_2$, $R_3$, $R_4$ and $R_5$, while the remaining four other substituents are hydrogen.

Thus for example, if R' corresponds to $R_1$, while $R_2$, $R_3$, $R_4$ and $R_5$ are hydrogen.

According to formula (IIb), R' and R" represent two of $R_1$, $R_2$, $R_3$, $R_4$ and $R_5$, while the remaining three substituents among $R_1$, $R_2$, $R_3$, $R_4$ or $R_5$ are hydrogen.

Thus for example, if R' corresponds to $R_1$ and R" corresponds to $R_2$, while $R_3$, $R_4$ and $R_5$ are hydrogen.

According to formula (IIIa), R' represents any one of $R_1$', $R_2$', $R_4$' and $R_5$', while the remaining three other substituents are hydrogen.

Thus for example, if R' corresponds to $R_1$', while $R_2$', $R_4$' and $R_5$' are hydrogen.

According to formula (IIIb), R' and R" represent two of $R_1'$, $R_2'$, $R_4'$ and $R_5'$, while the remaining two other substituents are hydrogen.

Thus for example, if R' corresponds to $R_1'$ and R" corresponds to $R_2'$, while $R_4'$ and $R_5'$ are hydrogen.

According to formula (IVa), R' represents any one of $R_1"$, $R_2"$, and $R_3"$ while the remaining two substituents among $R_1"$, $R_2"$, or $R_3"$ are hydrogen.

In a more particular embodiment, the corroles of the invention are corroles of type A2B, wherein $A_1$ and $A_2$ are different and respectively represented by one formula chosen from the formula (IIa), (IIb), (IIc), (IId), (IIIa), (IIIb), (IIIc), (IIId) or (IVa).

According to a still more particular embodiment, the invention concerns the corroles of formula (I) wherein:
M represents 3H;
$A_1$ and $A_2$ are different, and respectively represented by one formula chosen from the formula (IIa), (IIb), (IIc), (IId), (IIIa), (IIIb), (IIIc), (IIId) or (IVa) as defined above.

In another more particular embodiment, the corroles of the invention are corroles of type A3, wherein $A_1$ and $A_2$ are identical and respectively represented by one formula chosen from the formula (IIa), (IIb), (IIc), (IId), (IIIa), (IIIb), (IIIc), (IIId) or (IVa) as defined above.

According to another still more particular embodiment, the invention concerns the corroles of formula (I) wherein:
M represents 3H;
$A_1$ and $A_2$ are identical and represented by one of the formula chosen from the formula (IIa), (IIb), (IIc), (IId), (IIIa), (IIIb), (IIIc), (IIId) or (IVa) as defined above.

According to another embodiment, the corroles of the present invention are corroles having the phenyl groups $A_1$ and/or $A_2$ represented by one formula chosen from (IIe), (IIf), (IIg), (IIIe), or (IIIf):

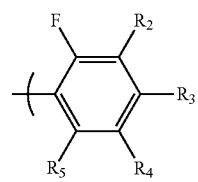

(IIe)

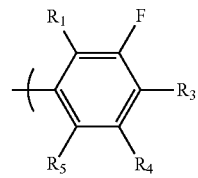

(IIf)

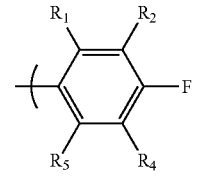

(IIg)

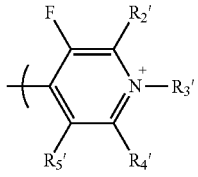

(IIIe)

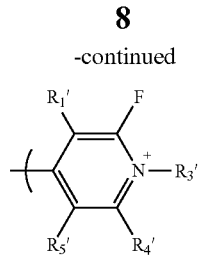

(IIIf)

or a pharmaceutically acceptable salt thereof, or an optical isomer thereof.

The substituents $R_1$, $R_2$, $R_3$, $R_4$, or $R_5$ in formulas (IIe), (IIf), (IIg) are as defined above for the formula II.

The substituents $R_1'$, $R_2'$, $R_3'$, $R_4'$, or $R_5'$ in formulas (IIe), (IIf), (IIg) are as defined above for the formula III.

Thus in this embodiment at least one of $A_1$ and $A_2$ or both of them are selected from (IIe), (IIf), (IIg), (IIIe), (IIIf). $A_1$ and $A_2$ may be identical or different.

In a more particular embodiment of the present invention, the corroles is chosen from following compounds:

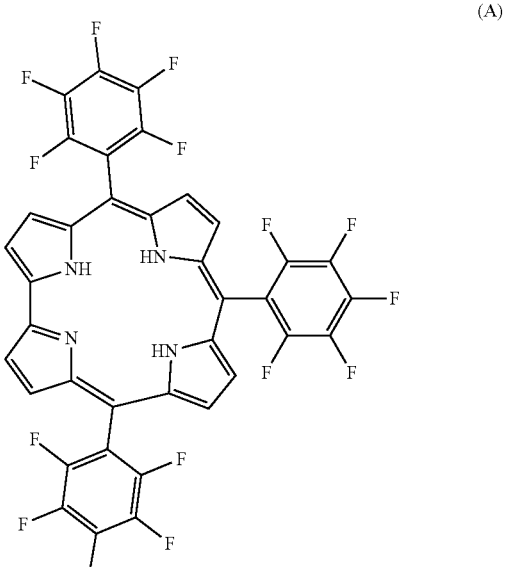

(A)

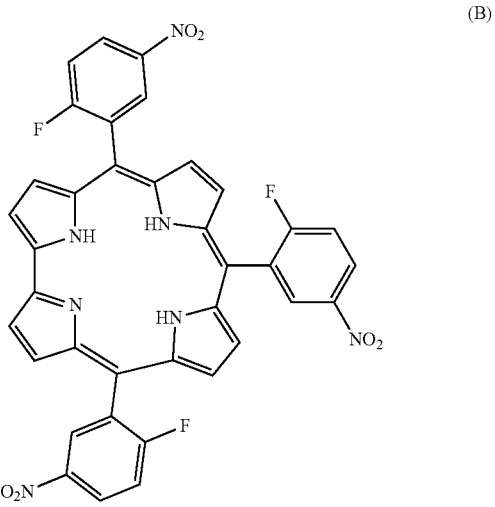

(B)

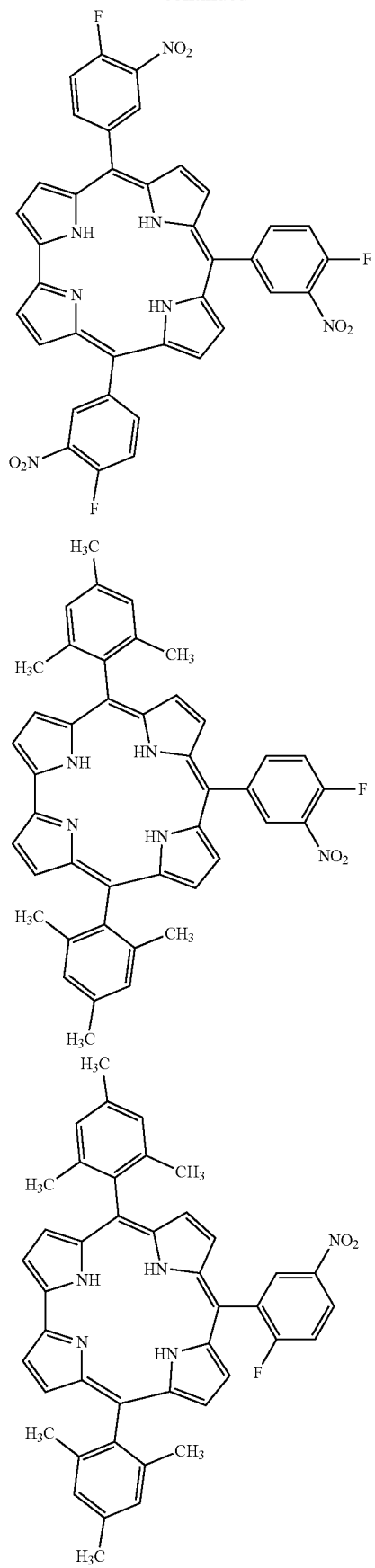
(C)
(D)
(E)
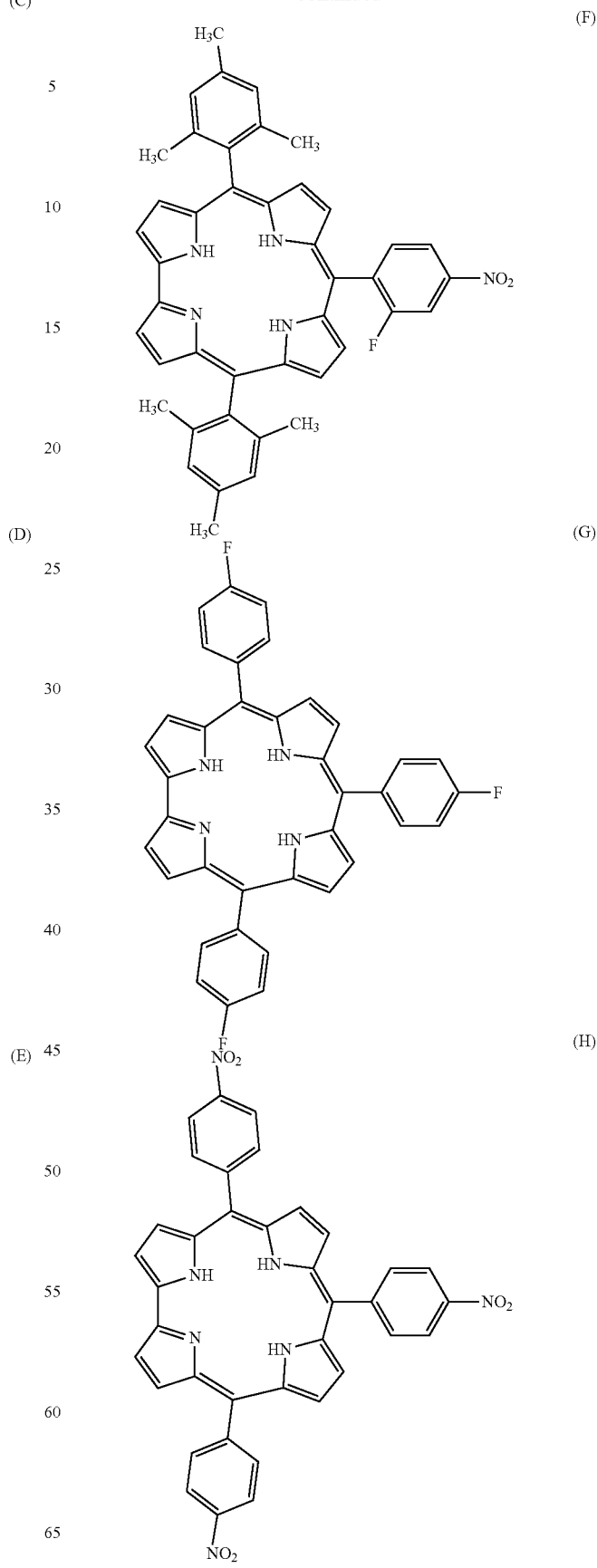
(F)
(G)
(H)

(I)
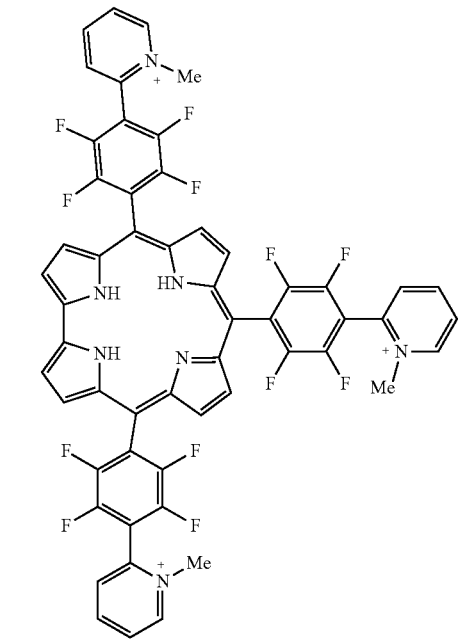
(J)
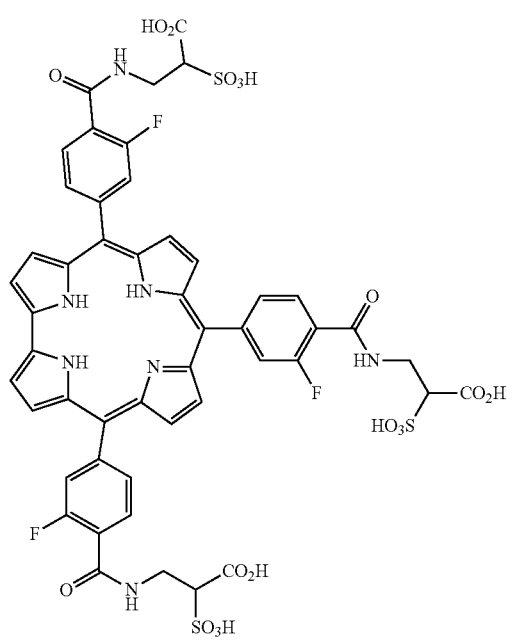
(K)
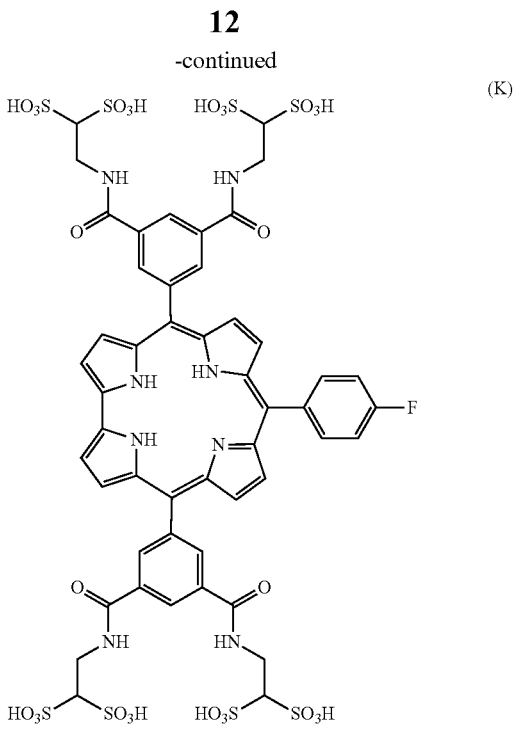
(L)
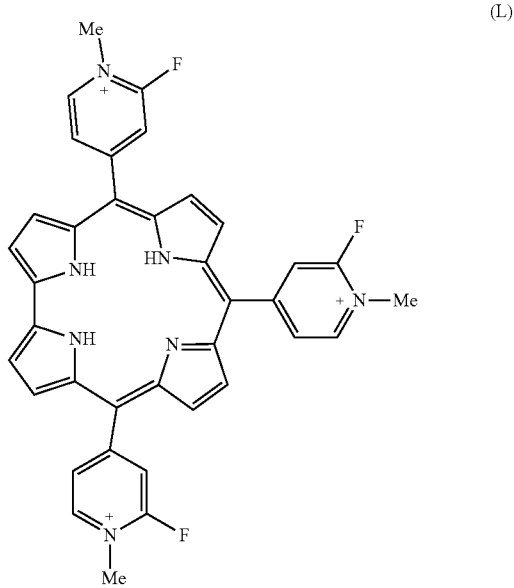
(M)
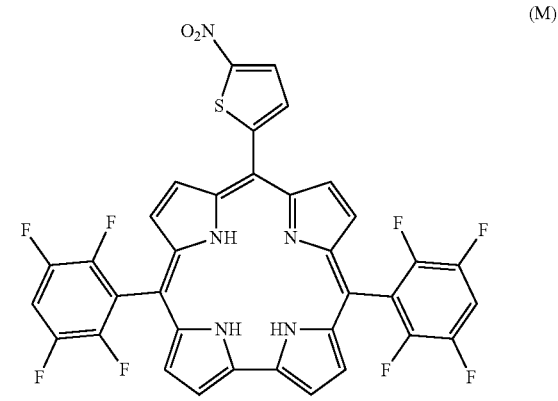

-continued

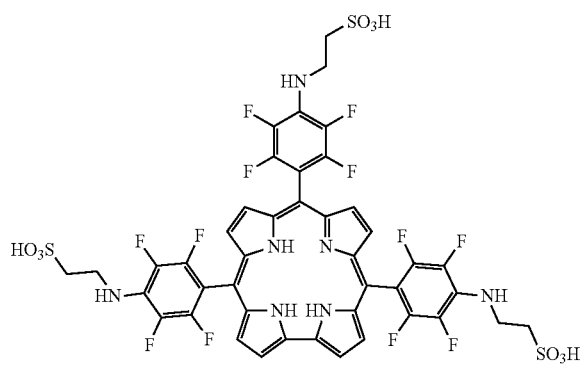

(N)

or a pharmaceutically acceptable salt thereof, or an optical isomer thereof.

Another subject-matter of the present invention concerns a pharmaceutical composition for its use in treating an infection of a poxvirus in human or non-human animals, comprising a corrole as defined above or a pharmaceutically acceptable salt thereof, or an optical isomer thereof, as active ingredient, and a pharmaceutically acceptable carrier.

The term "pharmaceutically acceptable carrier" means a carrier that is useful in preparing a pharmaceutical composition or formulation that is generally safe, non-toxic, and neither biologically nor otherwise undesirable, and includes a carrier that is acceptable for human or veterinary pharmaceutical use. The carrier can act as a vehicle, medium, or for dilution of the active ingredient. The formulation of the pharmaceutical composition of the present invention can be determined and carried out according to well-known prior art relating to drug formulation. The carrier material can be an organic or inorganic inert carrier material, for example one that is suitable for oral administration or injection. Suitable carriers include water, gelatin, arabic gum, lactose, starch, magnesium stearate, talc, vegetable oils, polyalkylene-glycols, glycerine and petroleum jelly. Additional additives such as flavoring agents, preservatives, stabilizers, emulsifying agents, buffers and the like may be added in accordance with accepted practices of pharmaceutical compounding.

The compositions can be in the form of tablets, pills, powders, lozenges, sachets, cachets, elixirs, suspensions, emulsions, solutions, syrups, soft and hard gelatin capsules, suppositories, sterile injectable solutions, and sterile packaged powders.

According to the formulation, the pharmaceutical composition of the present invention can be administrated by oral route or by injection.

Another subject-matter of the present invention concerns an association formed by:
 a corrole as defined above or a pharmaceutical acceptable salt thereof, or an optical isomer thereof,
 the active ingredient of another anti-poxvirus medicament chosen from an anti-poxvirus vaccine, or of any experimental medicament against poxvirus infection, for its use in the treatment of an infection by poxvirus in human or non-human animals.

In the present invention, the terms "medicament" and "drug" are interchangeable.

The term "active ingredient" is meant to the biologically active component of a medicament.

The present invention also relates to a combination product comprising:
 a corrole of as defined above or a pharmaceutical acceptable salt thereof, or an optical isomer thereof,
 another anti-poxvirus medicament, chosen from an anti-poxvirus vaccine, or of any experimental medicament against poxvirus infection. for its use simultaneously, separately, or sequentially in the treatment of an infection of poxvirus in humans or non-human animals.

The term "simultaneous use" is meant to be an administration of two active ingredients by the same route and at the same time.

The term "sequential use" is meant to be an administration sequentially on the time of two active ingredients by the same route.

The term "separate use" is meant to be an administration of 2 active ingredients at the same or substantially the same time by different routes.

The present invention provides also a method for treating the infections by poxvirus in humans or non-human animals, such as myxomatosis, cowpox, smallpox, sheeppox, orf, vaccinia, monkeypox, LSDV, or goatpox, comprising the step of:

Administrating a pharmaceutical effective amount of the aforementioned pharmaceutical composition to a human or a non-human animal suffering from an infection by poxvirus, such as myxomatosis, cowpox, smallpox, sheeppox, orf, vaccinia, monkeypox, LSDV, or goatpox. The term "pharmaceutically effective amount" means the amount of a before defined corrole or of a before defined combination product as pharmaceutical active in a pharmaceutical composition to produce the desired therapeutic effect.

The present invention is illustrated by the following figures and examples.

DESCRIPTION OF THE PREFERRED EMBODIMENTS

Examples

Figure 1:
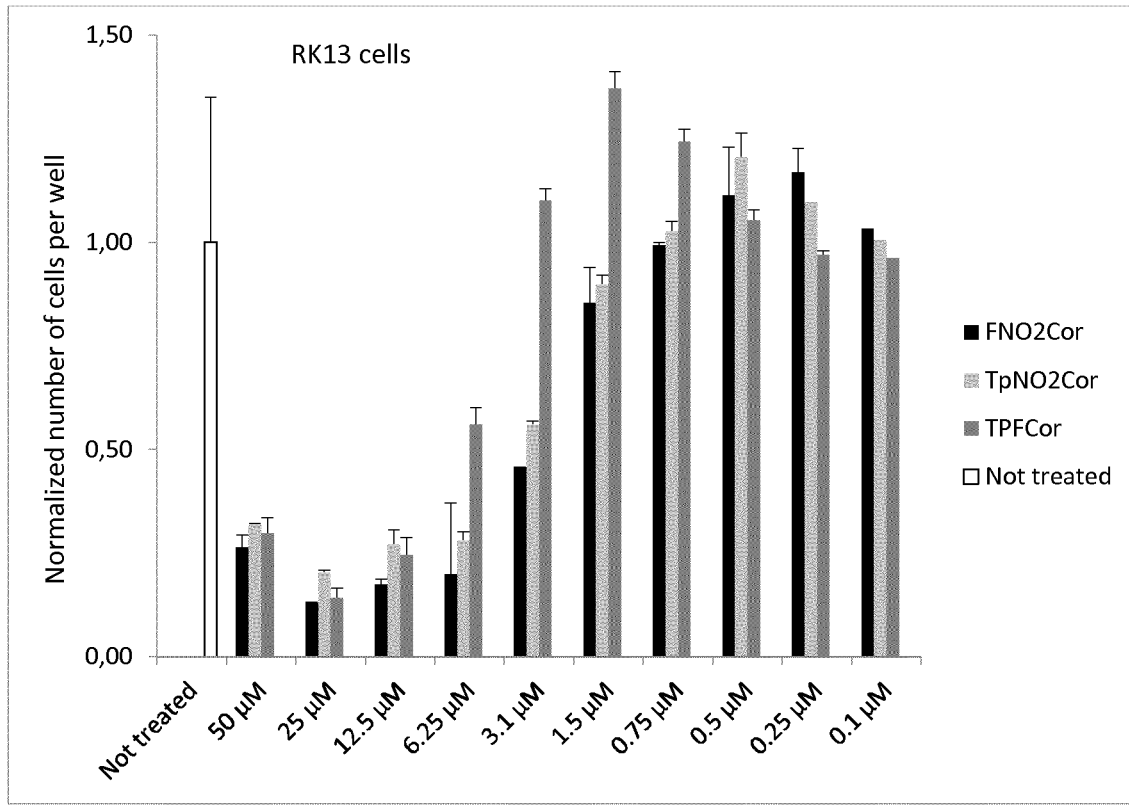
FIG. 1 shows the toxicity of compounds FNO2Cor, TpNO2Cor, TPFCor at different concentrations (0.1, 0.25, 0.5, 0.75, 1.5, 3.1, 6.25, 12.5, 25, 50 µM) on RK13 cells (rabbit epithelial kidney) seeded on a plate of 96 well. The Y axe shows normalized numbers of survived cells per well.

1. Materials and Methods
1.1 Preparation of Corroles of the Invention
All the chemical and solvents were of analytical grade and used without any further purification. Silica gel 60 (70-230 and 230-400 mesh, Sigma Aldrich) were used for column chromatography. Reactions were monitored by thin layer chromatography, UV-Vis spectroscopy and mass spectrophotometry. Chromatographic purification on column was performed on silica gel 60 (70-230 mesh, Sigma Aldrich. $^1$H NMR spectra were recorded on a Bruker AV300 spectrometer (300 MHz). CDCl$_3$ was used as solvent (except when indicated) and TMS as internal reference; the chemical shifts (δ) are given in ppm relative to residual CHCl$_3$ (7.26 ppm). All data were processed with TopSpin. MALDI/TOF mass spectra were recorded on Bruker Ultraflex Extreme MALDI Tandem TOF Mass Spectrometer. UV-vis spectra were measured on a Cary 50 spectrophotometer using CH$_2$Cl$_2$, CHCl$_3$ or THF as solvent.

General procedure #1 according to a modified Paolesse's method (Paolesse et al., *J. Org. Chem.* 2001, 66 (2), 550-556.).

Aldehyde (40.4 mmol) and distilled pyrrole (121 mmol) were dissolved in AcOH (500 mL) and the reaction was stirred at reflux for 3 h. The reaction mixture was cooled at room temperature and AcOH was evaporated under vacuum. The crude product was filtered over a chromatography column (silica, CH$_2$Cl$_2$). All fractions containing corrole (green fraction) were combined and evaporated to dryness. Purification details for each compound are described below.

Preparation of 5,10,15-Tris(4-nitrophenyl)corrole (Designed as TpNO2Cor)

This corrole corresponds to the above described compound H.

This corrole was prepared as described for general procedure 1 starting from 4-nitrobenzaldehyde and pyrrole. The residue was purified by chromatography column (alumina, CH$_2$Cl$_2$/heptane, 1/1, v/v) to give pure corrole (492 mg, 5.5%). UV-Vis (DCM): $\lambda_{max}$ (nm) (ε×10$^{-3}$ L mol$^{-1}$ cm$^{-1}$)=447 (53.4), 598 (18.7). $^1$H NMR (300 MHz, 300 K, DMSO-d6) δ (ppm): 8.41 (m, 2H), 8.58-8.71 (m, 14H), 8.87 (m, 2H), 9.14 (m, 2H). MS (MALDI-TOF) m/z=661.92 [M+H]$^+$, 661.17 calcd for C$_{37}$H$_{23}$N$_7$O$_5$. MS (ESI) m/z=660.15 [M–H]$^-$, 662.14 [M+H]$^+$, 661.17 calcd for C$_{37}$H$_{23}$N$_7$O$_5$.

Preparation of 5,10,15-Tris(2-fluoro-5-nitrophenyl)corrole (Designed as FNO2Cor)

This corrole corresponds to the above described compound B.

This corrole was prepared as described for general procedure 1 starting from 2-fluoro-5-nitrobenzaldehyde and pyrrole. The residue was crystallized from CHCl$_3$/Heptane (3/1, v/v), separating the solution, containing corrole, from the porphyrin precipitate. Solvent was removed under vacuum and the crude was crystallized from THF/heptane 1:2 v/v to give pure dark green corrole crystals (76.1 mg, 3.2% yield). UV-Vis (THF): $\lambda_{max}$ (nm) (ε×10$^{-3}$ L mol$^{-1}$ cm$^{-1}$) 418 (103.2), 572, 610, 645. $^1$H NMR (300 MHz, CDCl$_3$), δ (ppm): 9.11-9.00 (m, 5H), 8.73-8.61 (m, 5H), 8.50-8.47 (m, 4H), 7.71-7.62 (m, 3H), −2.83 (brs, 3H). MS (MALDI/TOF): m/z 715.007 [M]$^+$; 715.14 calcd for C$_{37}$H$_{20}$F$_3$N$_7$O$_6$.

General procedure #2 according to a modified Gryko's method (Gryko, D. T.; Koszarna, B. *Org. Biomol. Chem.*, 2003, 1(2), 350-357).

Aldehyde (20.0 mmol) was dissolved in distilled pyrrole (30.0 mmol) at room temperature and then a solution of TFA in CH$_2$Cl$_2$ (18 μL in 2.0 mL) was added and vigorously stirred. After 10 min, 800 mL of CH$_2$Cl$_2$ was added and stirred for further 1 h. DDQ (24.0 mmol) was added and stirred for another 1 h and solvent was removed under vacuum. The crude product was filtered over a chromatography column (silica, CH$_2$Cl$_2$). Purification details for each compound are described below.

Preparation of 5,10,15-Tris(pentafluorophenyl)corrole (Designed as TPFCor)

This corrole correspond to the above described compound of formula A.

This corrole was prepared as described for general procedure 2 starting from pentafluorobenzaldehyde and pyrrole. The residue was purified by a second column chromatography (silica, toluene/heptane, 8/2, v/v) to give pure dark green corrole crystals (228 mg, 4.3% yield). UV-Vis (THF): $\lambda_{max}$ (nm) (ε×10$^{-3}$ L mol$^{-1}$ cm$^{-1}$) 407 (150.1), 562 (23.9), 604 (12.4). $^1$H NMR (300 MHz, CDCl$_3$), δ (ppm): 9.10 (d, J=4.2 Hz, 2H), 8.79 (d, J=4.8 Hz, 2H), 8.60 (4H), 2.88 (brs, 3H). $^{19}$F NMR (282 MHz, CDCl$_3$) 137.2 (2F), 137.7 (4F), 152.2 (2F), 152.8 (1F), 161.5 (4F), 161.9 (2F). MS (MALDI/TOF): m/z 796.91 [M+H]$^+$, 796.07 calcd for C$_{37}$H$_{11}$F$_{15}$N$_4$.

1.2 MYXV Infection

RK13 (rabbit epitelial kidney) cells were used for MYXV infection assay.

Cells were grown in 200 μL Dulbecco's Modified Eagle's medium (DMEM) without phenol red (Sigma-Aldrich), 10% SVF, Pen-strep, 1× sodium pyruvate, 1× Glutamax.

Infection Protocol

MYXV-GFP infection was carried out on RK13 cells seeded in 96 wells plate, in triplicate at two multiplicity of infection (MOI) and 7 concentrations of FNO2Cor, TPFCor, TpNO2Cor.

D0: RK13 cells seeded at 6 k per well in Corning Glass Bottom 96 well plates in 200 μL of DMEM without phenol red.

D1: cells are treated with FNO2Cor, TpNO2Cor, TPFCor (from 50 to 0.1 μM by two fold dilution) in duplicate for the toxicity study.

In parallel: cells are treated with FNO2Cor, TpNO2Cor, TPFCor (from 6.25 to 0.08 μM by two fold dilution) and are infected at different multiplicity of infection (MOI) in triplicate: MYXV at MOI 0.5 or 0.01.

1.3 Toxicity Assessment

The toxicity of compounds FNO2Cor, TpNO2Cor or TPFCor on ARPE-19 cells was evaluated after 6 days of treatment. 10 concentrations (50, 25, 12.5, 6.25, 3.1, 1.5, 0.75, 0.5, 0.25, 0.1 μM) of FNO2Cor, TpNO2Cor and TPFCor were studied.

1.4 Microscopy

RK13 cells at MOI 0.5 48 h post-infection (PI) are fixed with Formalin 10 min at room temperature. Wash with 200 μL PBS and 100 μL PBS/Hoechst 33342 (1/1000) per well. 96 well plates are kept at 4° C. in the dark until data acquisition. Image acquisition and analysis for high content quantification is performed on a Thermo Cellomics Arrayscan VTI microscope using a modified compartmental analysis algorithm.

RK13 cells for the toxicity study and RK13 cells at MOI 0.01 6 days PI are fixed and image acquisition and analysis are performed as previously described.

On 48 h and 6d post-infection, data acquisition was done by high content microscopy to calculate infection level according to compound concentration.

2. Results 2.1 Cytotoxicity

Cytotoxicity of compounds FNO2Cor, TPFCor and TpNO2Cor were assessed at different concentration on RK13 cells according to the method described on section 1.3. $CC_{50}$ values of these three compounds on RK13 cells are given in table I below.

TABLE I

| | FNO2Cor | TpNO2Cor | TPFCor |
|---|---|---|---|
| $CC_{50}$ RK13 | 3.74 | 4.36 | 6.68 |

FIG. 1 and Table I show that three tested compounds are safe for rabbit epithelial kidney cells at low concentrations.

2.2 Antiviral Activity

Figure 2:
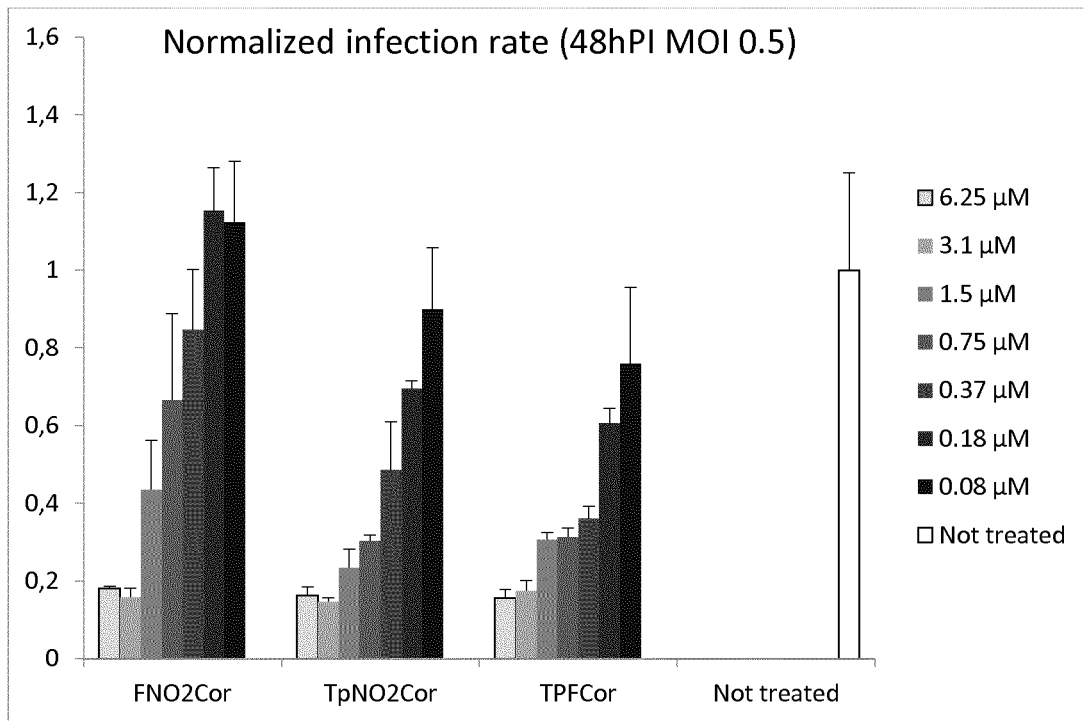
FIG. 2 shows normalized infection rate of MYXV in RK13 cells at multiplicity of infection (MOI) 0.5 after 48 h post-infection by compounds FNO2Cor, TpNO2Cor, or TPFCor, at different concentrations (0.08, 0.18, 0.37, 0.75, 1.5, 3.1, 6.25 µM).
Figure 3:
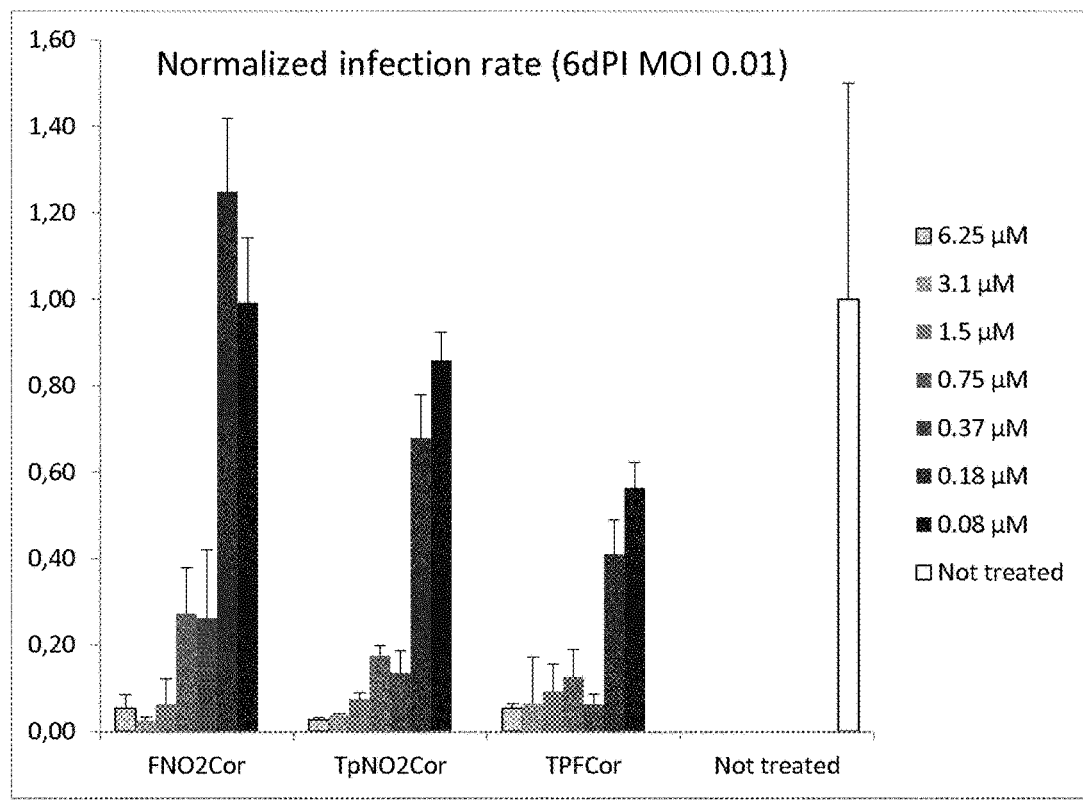
FIG. 3 shows normalized infection rate of MYXV in RK13 cells at multiplicity of infection (MOI) 0.01 after 6 days post-infection by compounds FNO2Cor, TpNO2Cor, or TPFCor, at different concentrations (0.08, 0.18, 0.37, 0.75, 1.5, 3.1, 6.25 µM).
Figure 4:
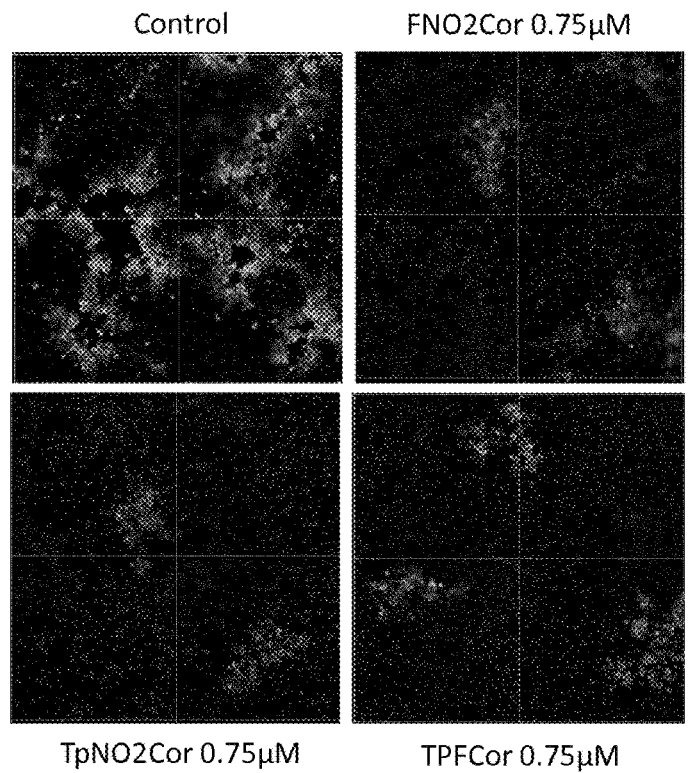
FIG. 4 shows lysis plaques in RK13 infected with MYXV 6d PI observed by microscope.

Compounds FNO2Cor, TPFCor, and TpNO2Cor were assessed at 7 different concentrations in RK13 cell culture on 48 h post-infection (FIG. 2) or on 6 days post-infection (FIG. 3) to evaluate their activity for inhibiting MYXV infection. Table II displays $IC_{50}$ values of these three compounds on RK13 cells on 48 h or 6d PI. The selectivity index of these compounds are displayed in table III.

TABLE II

| | FNO2Cor | TpNO2Cor | TPFCor |
|---|---|---|---|
| IC50 (48 h PI) | 1.33 | 0.43 | 0.27 |
| IC50 (6 d PI) | 0.50 | 0.20 | 0.12 |

TABLE III

| | FNO2Cor | TpNO2Cor | TPFCor |
|---|---|---|---|
| SI (48 h PI) | 2.81 | 10.25 | 24.40 |
| SI (6 d PI) | 7.52 | 21.45 | 55.31 |

These results indicate that all three tested compounds can inhibit MYXV infection rate in RK13 cells. TPFCor and TpNO2Cor have better in vitro anti-MYXV effect than FNO2Cor.

2.3 Lysis Plaques Analysis

Lysis plaque analysis was carried out in RK13 infected with MYXV 6d PI. Lysis plaques area and number of lysis plaques were assessed directly on microscope pictures (FIG. 4). The results are also displayed in table IV.

TABLE IV

| | Area in $cm^2$ of lysis plaques | | | | | Number of lysis plaques | | | | |
|---|---|---|---|---|---|---|---|---|---|---|
| Concentration µM | 0 | 3.1 | 1.5 | 0.75 | 0.37 | 0 | 3.1 | 1.5 | 0.75 | 0.37 |
| Not treated | 7.6 | | | | | 19 | | | | |
| FNO2Cor | | nd | nd | 3.4 | 8 | | 0 | 1.3 | 6 | 5 |
| TpNO2Cor | | nd | nd | 3.4 | 9 | | 0 | 2.7 | 6.7 | 4 |
| TPFCor | | | | | 6 | | 4 | 3.3 | 6 | 6.7 |

These results show that three tested compounds can prevent cell to cell propagation of MYXV infection.

The invention claimed is:

1. A method for treatment of an infection of a poxvirus in human or non-human animals, comprising providing a corrole of type A3 or A2B of formula (I):

(I)

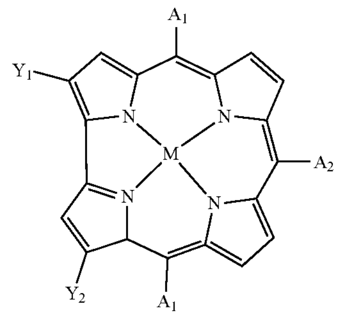

wherein:

$Y_1$ and $Y_2$ are identical or different and each independently chosen from, —H, —$SO_3H$, —$SO_3^-$, —$NO_2$, —CHO, —$NH_2$, —$NH_3^+$, —COOH, —$COO^-$ M represents 3H or a metal chosen from the group of Cu, Mn, Fe, Co, V, Cr, Ti, Ag, Rh, Ru, Mo, Zr, Au, Pt, Ir, Re, W, Hf, Li, Al, Ga, Ge, Sn, As, Sb, Pb, Bi, La, Gd, Tb, or Th $A_1$ and $A_2$ are identical or different and each represents a phenyl group of formula (II), (II)

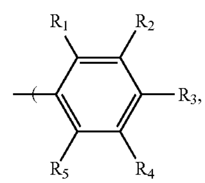

or

A pyridinium group of formula (III)

(III)

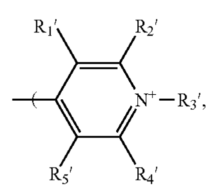

or a five membered heterocycle of formula (IV)

(IV)

with each of $R_1$, $R_2$, $R_3$, $R_4$ and $R_5$ of formula (II); each of $R_1'$, $R_2'$, $R_4'$ and $R_5'$ of formula (III); each of $R_1''$, $R_2''$, and $R_3''$ of formula (IV) being chosen from:

(a). —H, —CN, —$NO_2$, —CHO, —$SO_3H$, —OH, —SH, —C≡CH, —$NH_2$, —COOH, —$CONH_2$, (b). a halogen atom, selected from a chlorine atom, a fluorine atom, a bromine atom, or an iodine atom, (c). a (C$_1$-C$_8$) alkyl chain,
(d). a PEG chain of formula —(CH$_2$—CH$_2$—O)$_n$—H or of formula —(CH$_2$—CH$_2$—O)$_n$—CH$_3$, wherein n is an integer chosen from 1, 2, 3, 4 or 5,
(e). —CX$_3$, X being a halogen atom selected from a chlorine atom, a fluorine atom, a bromine atom, or an iodine atom,
(f). —OR$_a$, —NR$_a$R$_b$, —NHR$_a$, —COOR$_a$, —CONHR$_a$, —CONR$_a$R$_b$, —SO$_2$R$_a$, —COR$_a$, —SR$_a$, —C≡CR$_a$, R$_a$ and R$_b$ being independently chosen from —(CH$_2$—CH$_2$—SO$_3$H), a (C$_1$-C$_8$) alkyl chain, a PEG chain of formula —(CH$_2$—CH$_2$—O)$_n$—H, or of formula —(CH$_2$—CH$_2$—O)$_n$—CH$_3$, wherein n is an integer chosen from 1, 2, 3, 4 or 5
(g). a group of formula

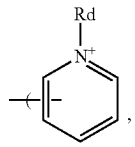

wherein R$_c$ is —COOH, or —SO$_3$H,
(h). a pyridinium group of formula

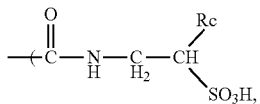

wherein R$_d$ is a (C$_1$-C$_8$) alkyl chain, or —(CH$_2$)$_n$SO$_3^-$, n being an integer chosen from 1, 2, 3, 4 or 5,
R$_3$' of formula (III) being chosen from
—H, —CONH$_2$,
a (C$_1$-C$_8$)alkyl
a PEG chain of formula —(CH$_2$—CH$_2$—O)$_n$—H or of formula —(CH$_2$—CH$_2$—O)$_n$—CH$_3$, wherein n is an integer chosen from 1, 2, 3, 4 or 5,
a group —(CH$_2$)$_n$SO$_3^-$, n being an integer chosen from 1, 2, 3, 4 or 5
—OR$_a$, —NR$_a$R$_b$, —NHR$_a$, —COOR$_a$, —CONHR$_a$, —CONR$_a$R$_b$, —COR$_a$, R$_a$ and R$_b$ being independently chosen from —(CH$_2$—CH$_2$—SO$_3$H), a (C$_1$-C$_8$) alkyl chain, a PEG chain of formula —(CH$_2$—CH$_2$—O)$_n$—H, or of formula —(CH$_2$—CH$_2$—O)$_n$—CH$_3$ wherein n is an integer chosen from 1, 2, 3, 4 or 5,
E of formula (IV) is chosen from —O—, —S—, —Se—, —NH—,
or a pharmaceutically acceptable salt thereof, or an optical isomer thereof, and administering an effective amount of the corrole to the human or non-human animals.

2. The method of claim 1, wherein the poxvirus is belonging to the subfamily Chordopoxvirinae or subfamily Entomopoxvirinae.

3. The method of claim 1, for wherein the infection of a poxvirus is myxomatosis, cowpox, smallpox, sheeppox, orf, vaccinia, monkeypox, LSDV, goatpox or an infection by any other members of the poxvirus family.

4. The method of claim 1, wherein the corrole is of formula (Ia)

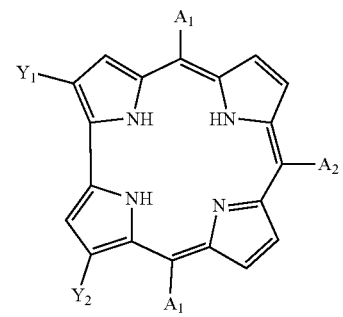

Wherein Y$_1$, Y$_2$, A$_1$ and A$_2$ are defined as in formula (I).

5. The method of claim 4, wherein A1 and/or A2 are represented by the formula (IIa), formula (IIb), formula (IIc), formula (IId), formula (IIIa), formula (IIIb), or formula (IIIc)

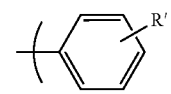

(IIa)

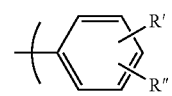

(IIb)

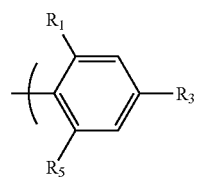

(IIc)

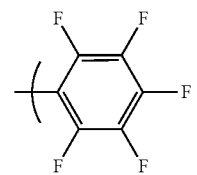

(IId)

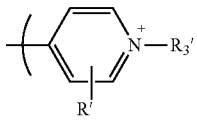

(IIIa)

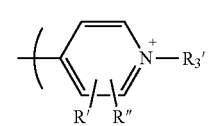

(IIIb)

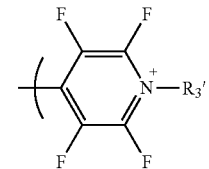

(IIIc)

-continued

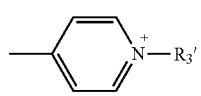
(IIId)

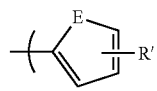
(IVa)

wherein R', R", $R_1$, $R_3$ and $R_5$ are independently chosen from:
—CN, —$NO_2$, —CHO, —$SO_3H$, —OH, —$NH_2$, —COOH, —$CONH_2$, —SH, —C≡CH,
a halogen atom, selected from a chlorine atom, a fluorine atom, a bromine atom, or an iodine atom,
a ($C_1$-$C_8$) alkyl chain,
a PEG chain of formula —($CH_2$—$CH_2$—O)$_n$—H or of formula —($CH_2$—$CH_2$—O)$_n$—$CH_3$, wherein n is an integer chosen from 1, 2, 3, 4 or 5,
—$CX_3$, X being a halogen selected from a chlorine atom, a fluorine atom, a bromine atom, or an iodine atom,
—$OR_a$, —$NR_aR_b$, —$COOR_a$, —$NHR_a$, —$CONR_aR_b$, —$CONHR_a$, —$SO_3R_a$, —$SO_2NHR_a$, —$COR_a$, —$SR_a$, —C≡$CR_a$, $R_a$ and $R_b$ being independently chosen from —($CH_2$—$CH_2$—$SO_3H$), a ($C_1$-$C_8$) alkyl chain, a PEG chain of formula —($CH_2$—$CH_2$—O)$_n$—H or of formula —($CH_2$—$CH_2$—O)$_n$—$CH_3$, wherein n is an integer chosen from 1, 2, 3, 4 or 5, a group of formula

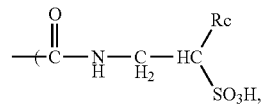

wherein $R_c$ is —COOH, or —$SO_3H$,
a pyridinium group of formula

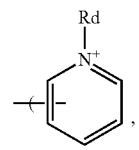

wherein $R_d$ is a ($C_1$-$C_8$) alkyl chain, or —($CH_2$)$_n$$SO_3^-$, n being an integer chosen from 1, 2, 3, 4 or 5.

6. The method of claim 5, wherein $A_1$ and $A_2$ are different and respectively represented by one formula chosen from the formula (IIa), (IIb), (IIc), (IId), (IIIa), (IIIb), (IIIc), (IIId) or (IVa).

7. The method of claim 5, wherein $A_1$ and $A_2$ are identical and represented by one formula chosen from the formula (IIa), (IIb), (IIc), (IId), (IIIa), (IIIb), (IIIc), (IIId) or (IVa).

8. The method of claim 1, wherein the corrole is chosen from following compounds

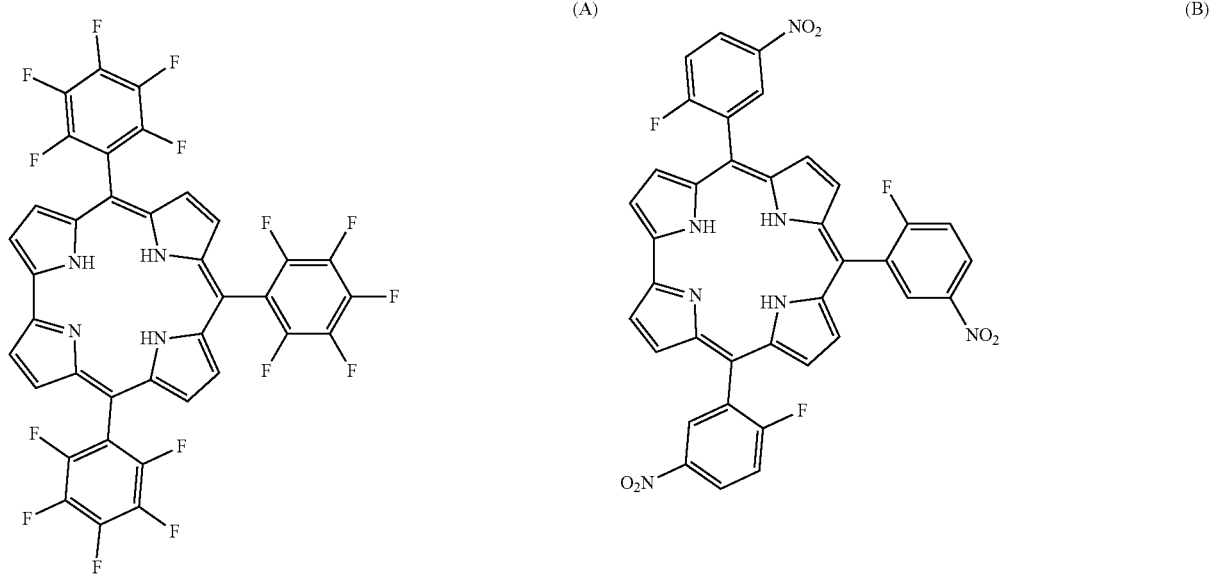

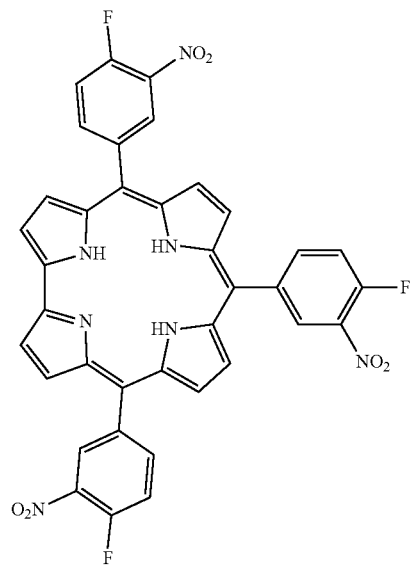
(C)
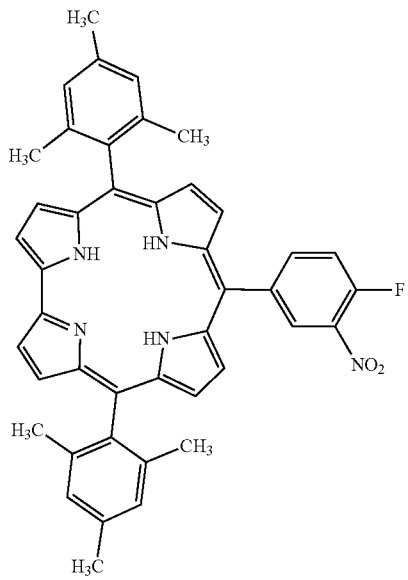
(D)
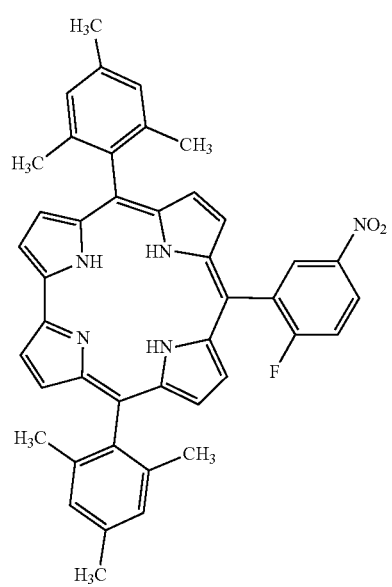
(E)
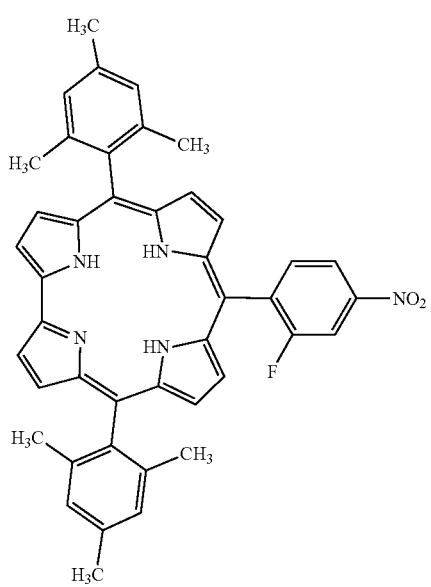
(F)

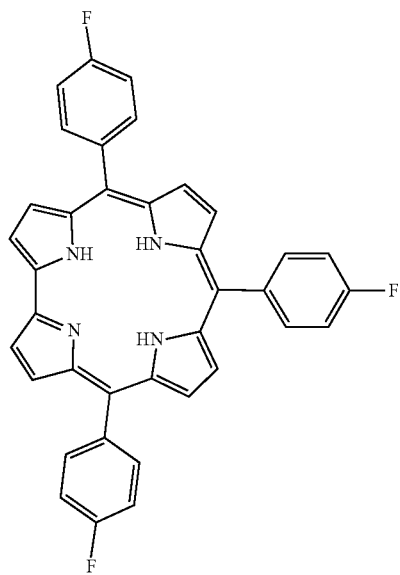
(G)
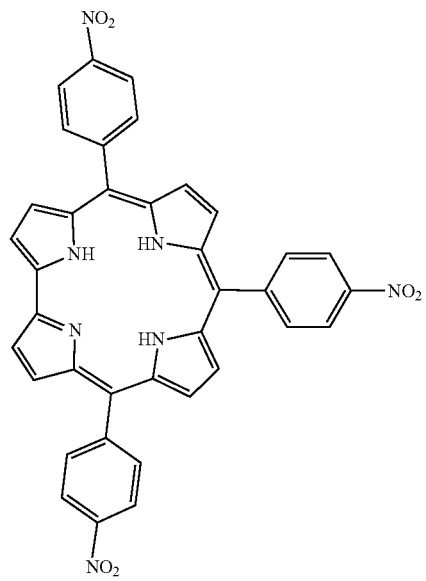
(H)
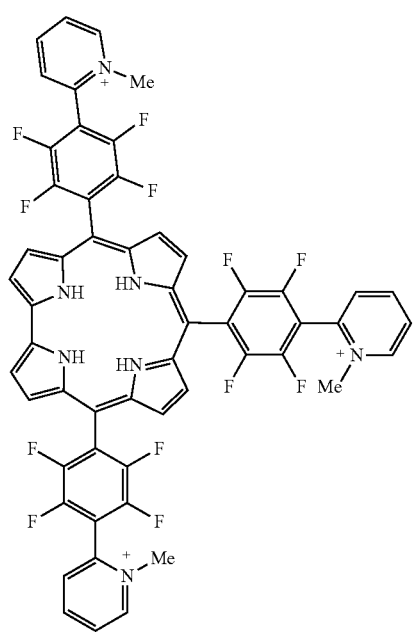
(I)
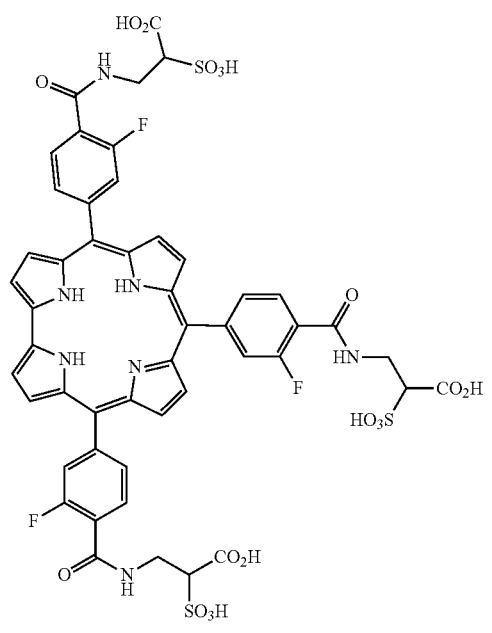
(J)

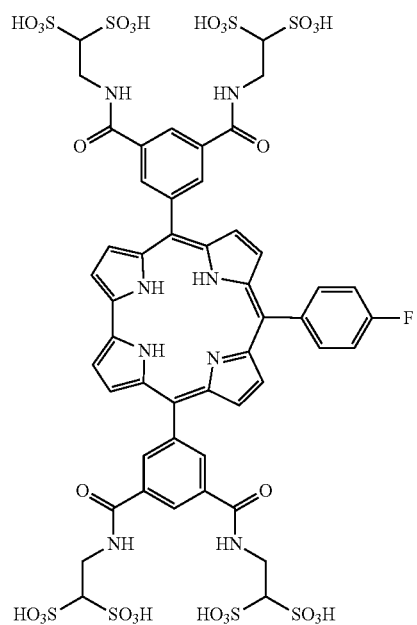
(K)
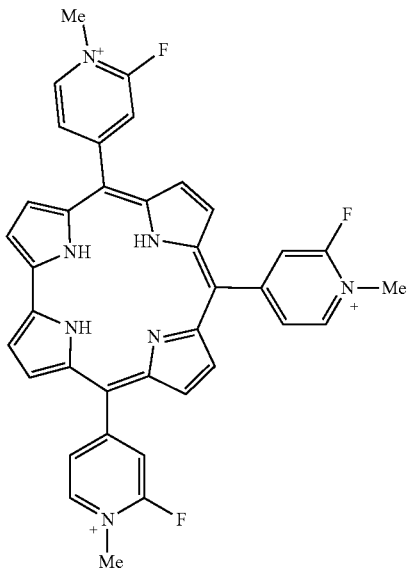
(L)
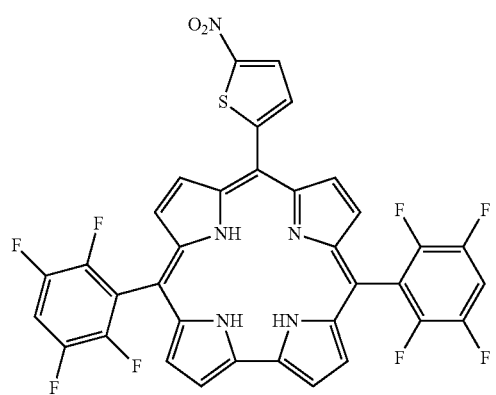
(M)
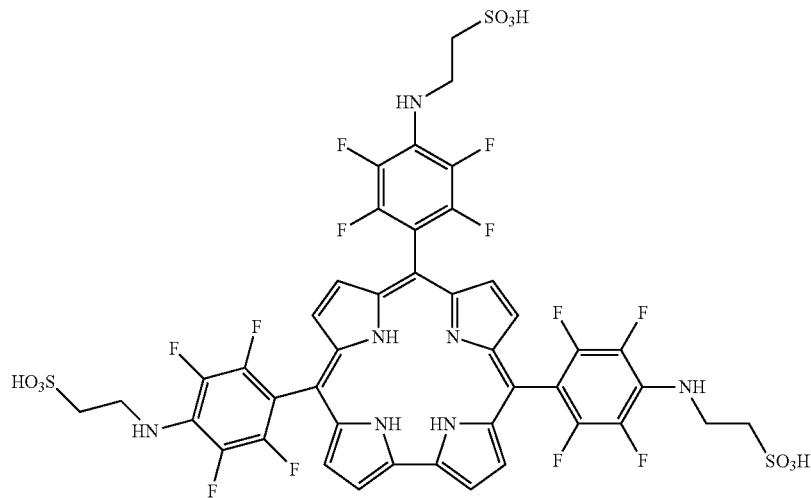
(N)
or a pharmaceutically acceptable salt thereof, or an optical isomer thereof.
9. The method of claim 2, wherein the corrole is of formula (Ia)

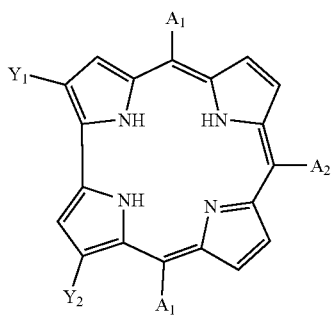
(Ia)
Wherein $Y_1$, $Y_2$, $A_1$ and $A_2$ are defined as in formula (I).
10. The method of claim 3, wherein the corrole is of formula (Ia)
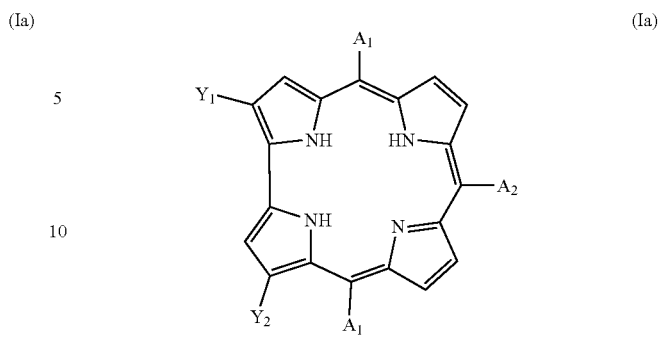
(Ia)
Wherein $Y_1$, $Y_2$, $A_1$ and $A_2$ are defined as in formula (I).
11. The method of claim 2, wherein the corrole is chosen from following compounds
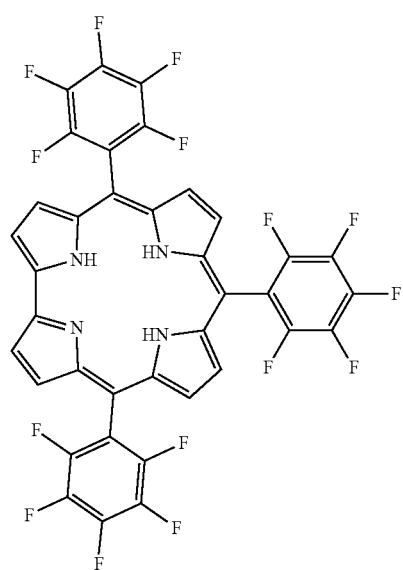
(A)
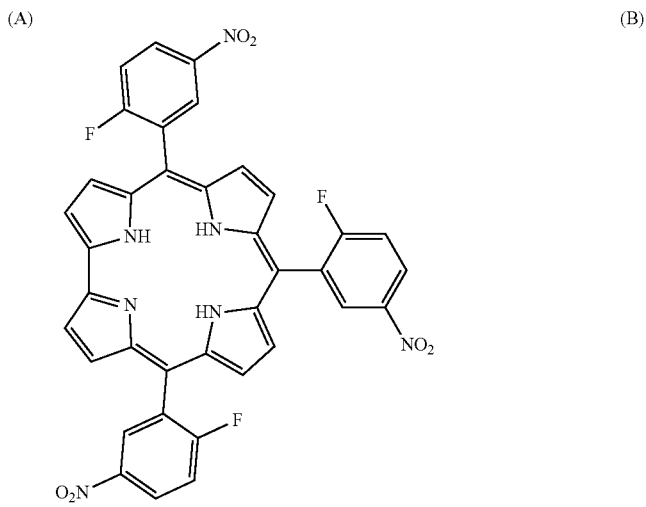
(B)
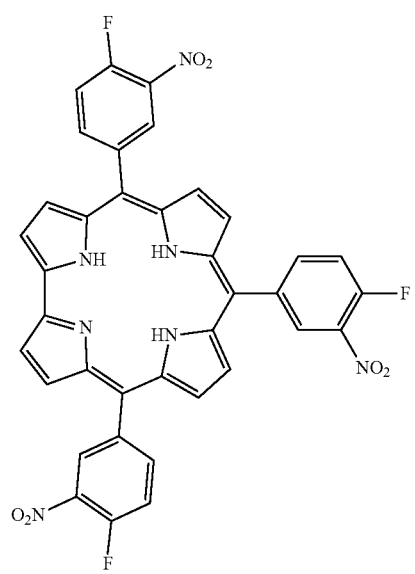
(C)
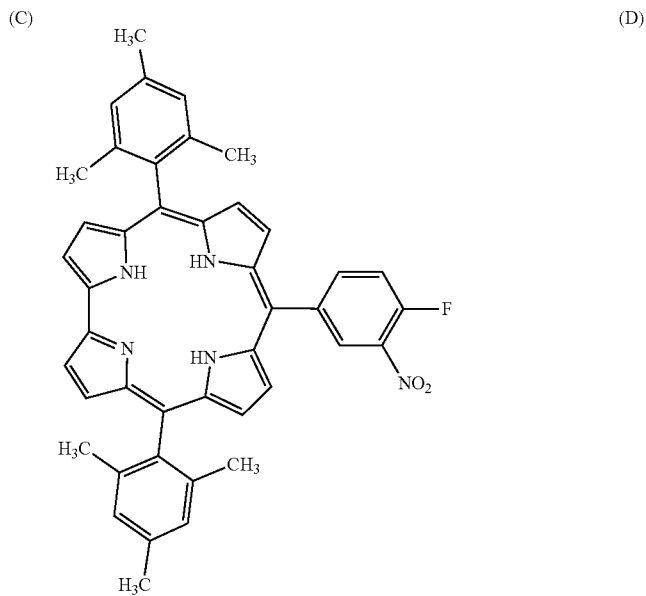
(D)

-continued
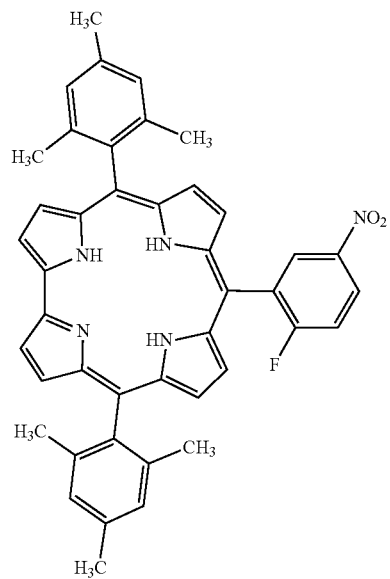
(E)
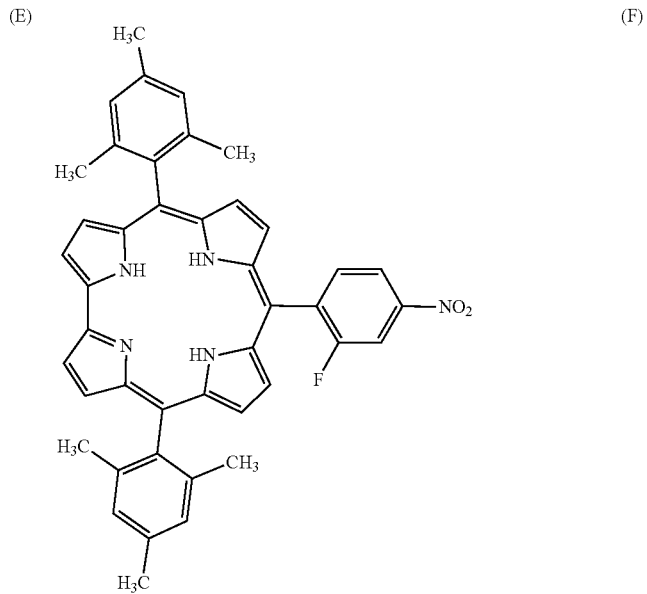
(F)
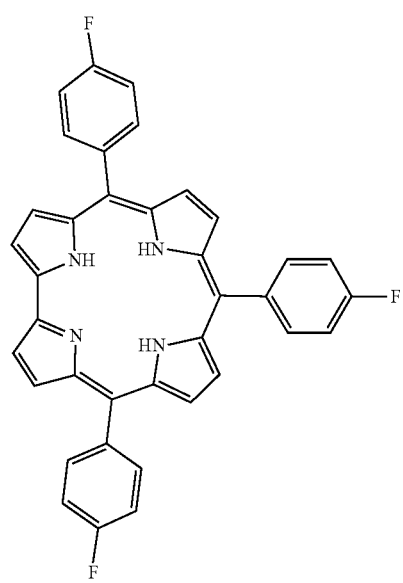
(G)
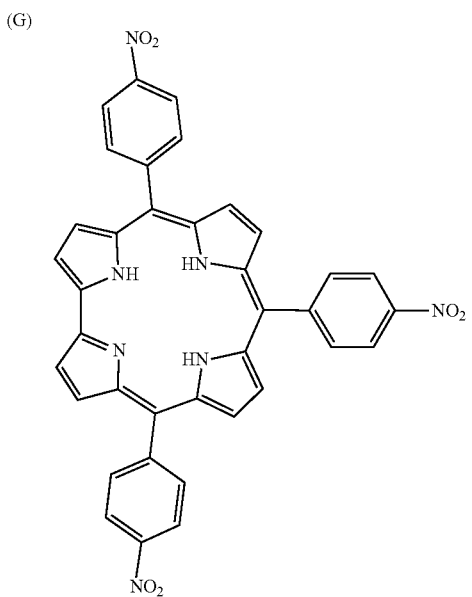
(H)

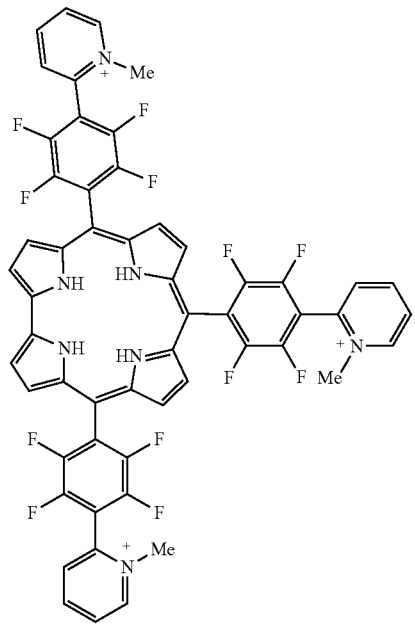
(I)
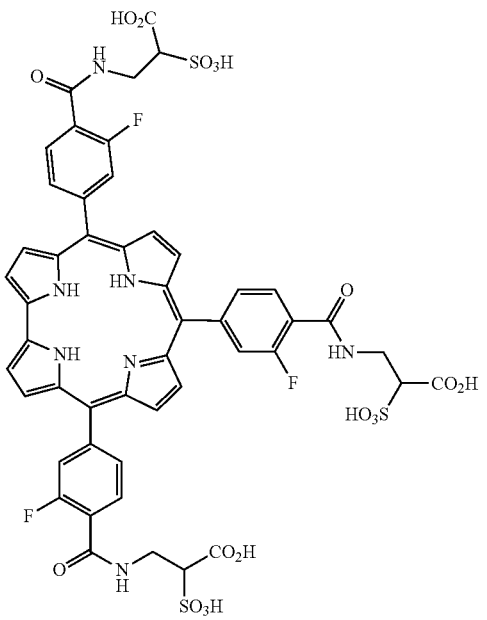
(J)
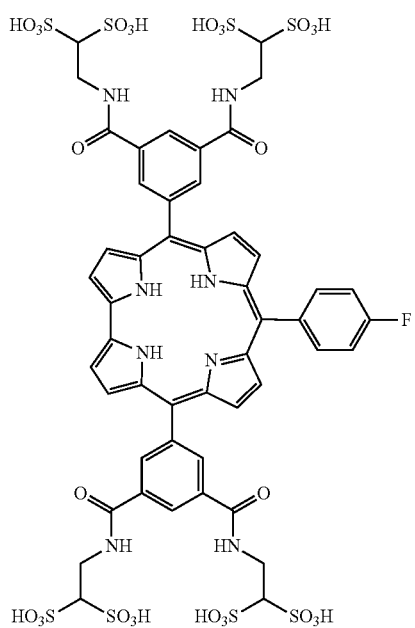
(K)
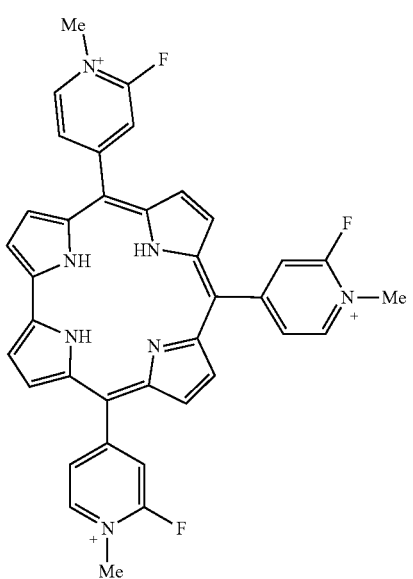
(L)
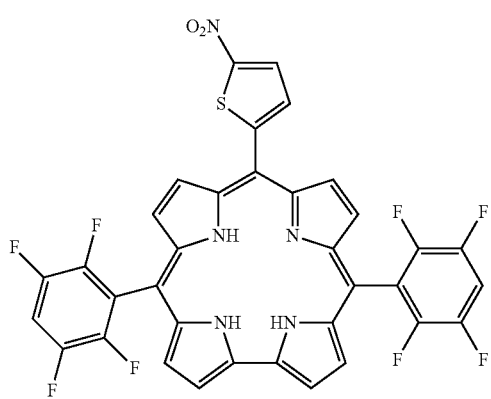
(M)

(N)
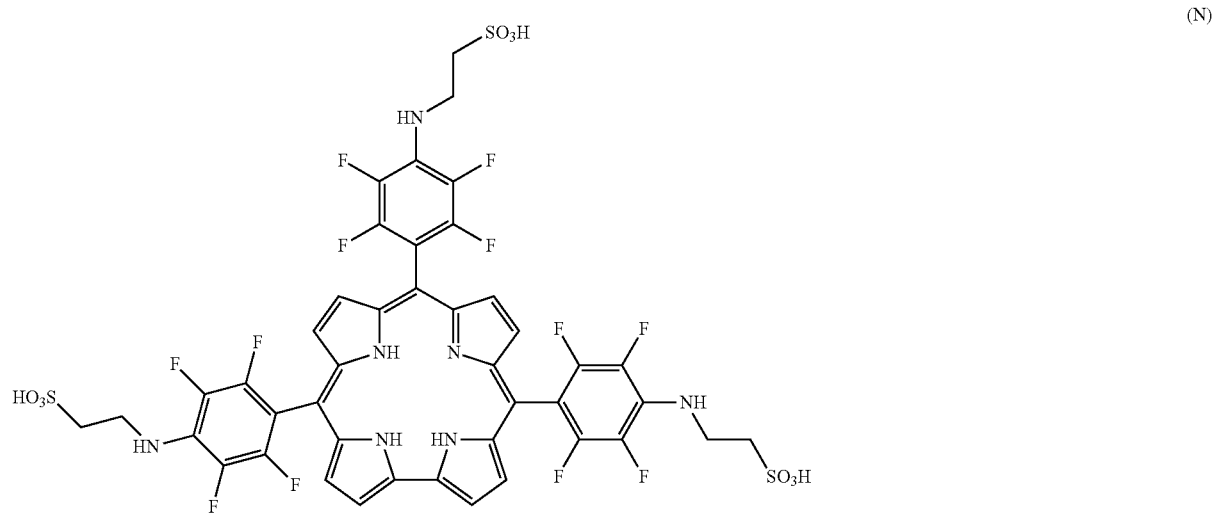
or a pharmaceutically acceptable salt thereof, or an optical isomer thereof.
12. The method of claim 3, wherein the corrole is chosen from following compounds
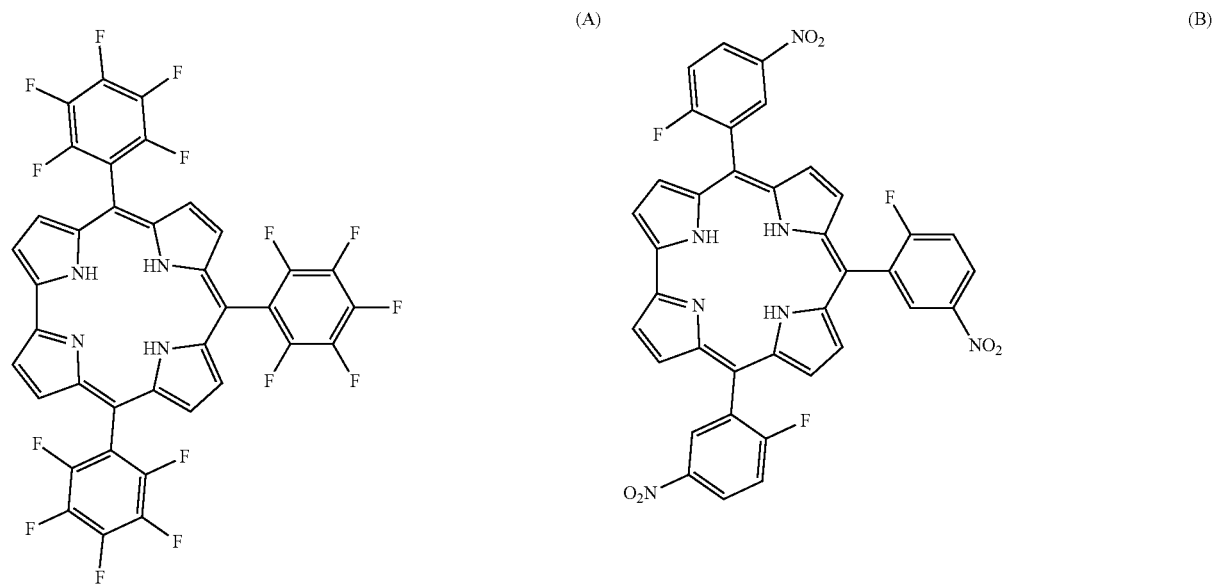

-continued
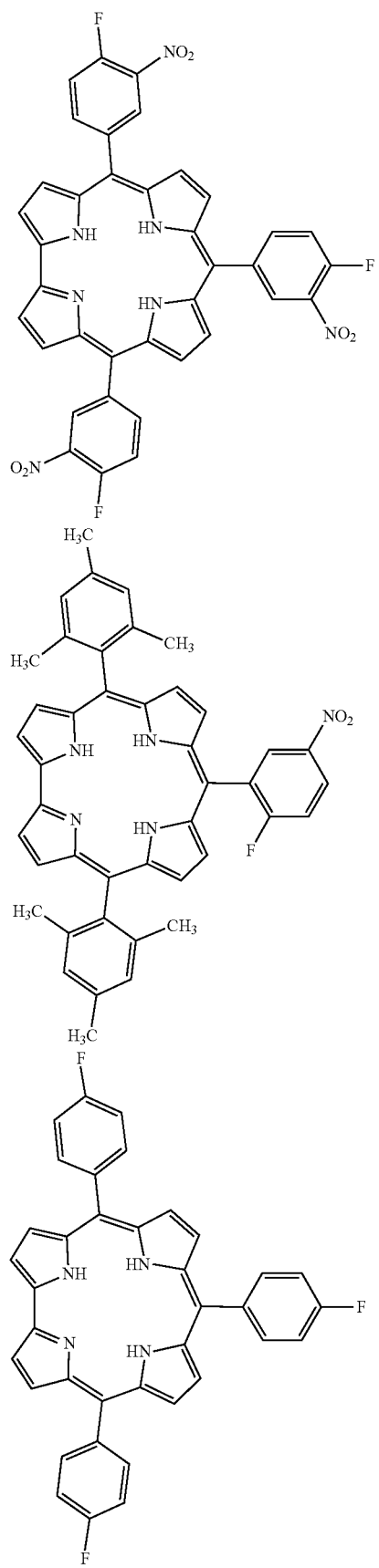
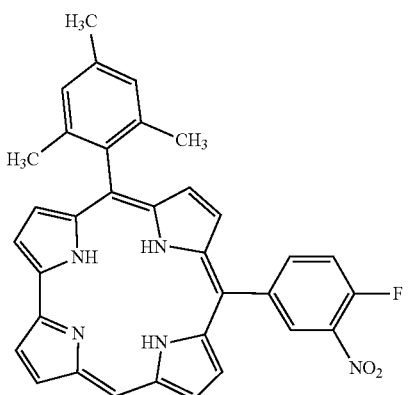
(C)
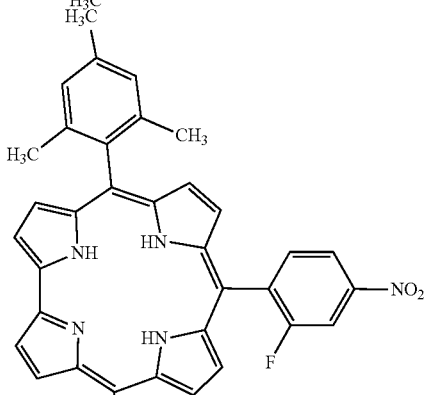
(E)
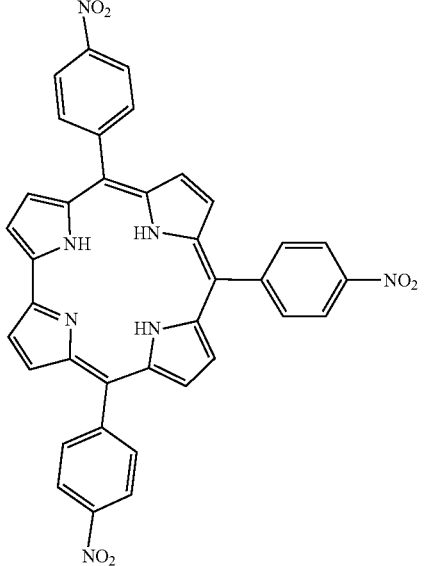
(G)
(D)
(F)
(H)

-continued
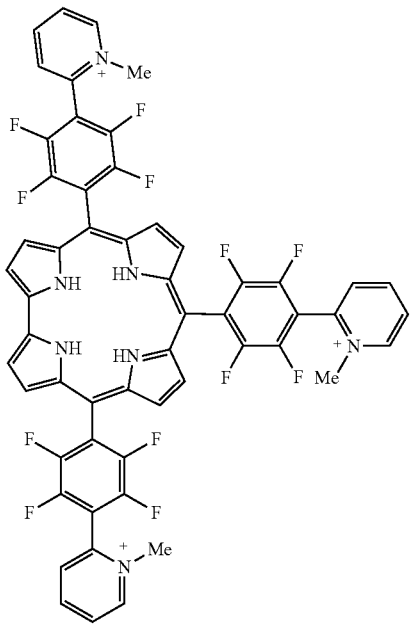
(I)
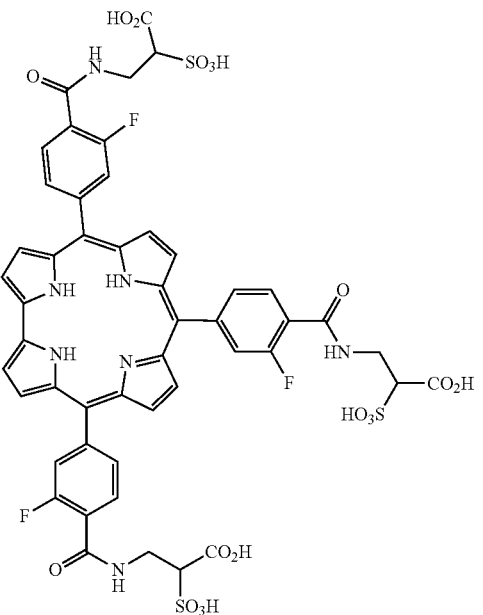
(J)
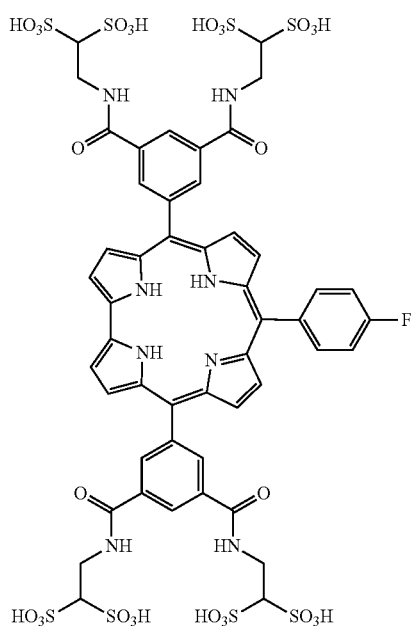
(K)
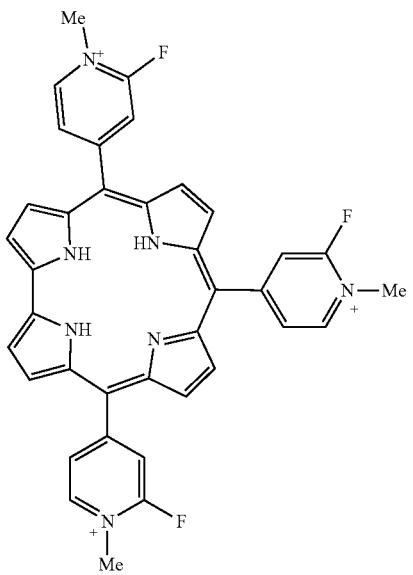
(L)
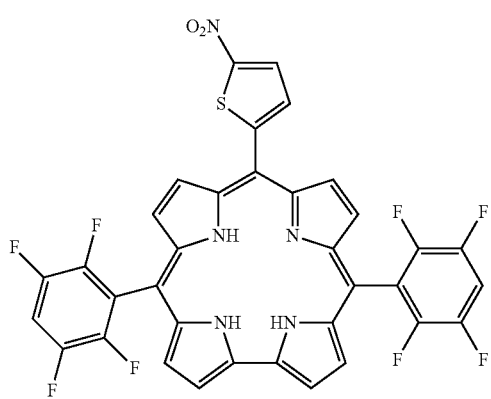
(M)

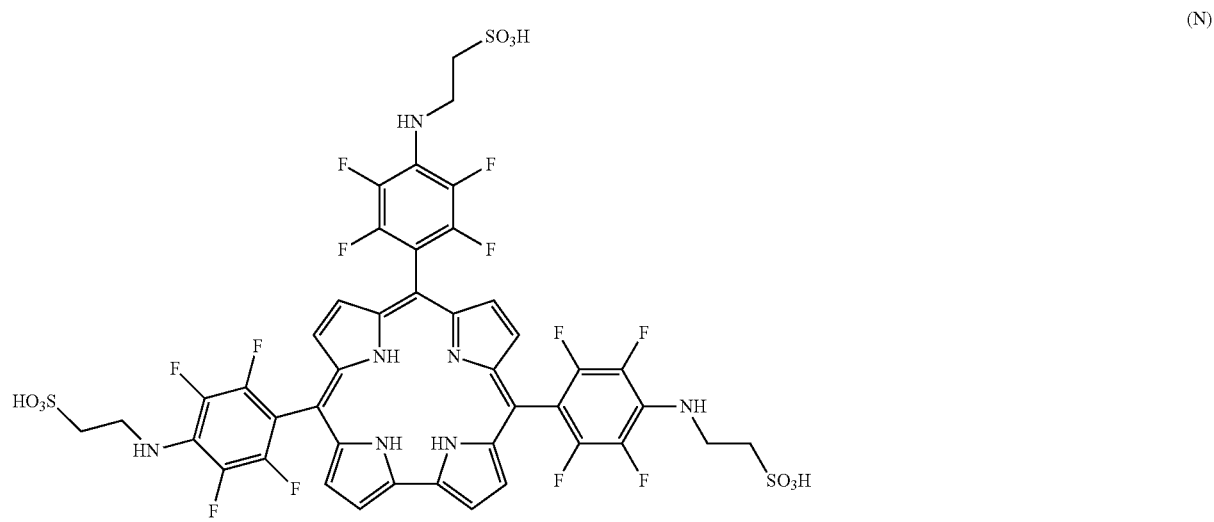
(N)
or a pharmaceutically acceptable salt thereof, or an optical isomer thereof.
13. The method of claim 4, wherein the corrole is chosen from following compounds
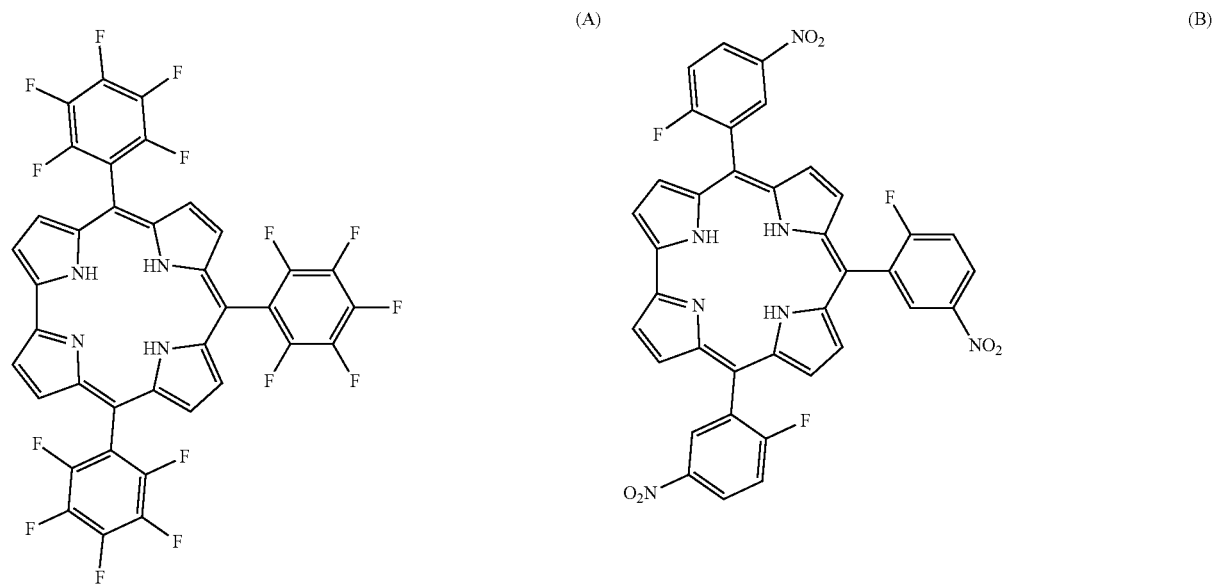
(A) (B)

-continued
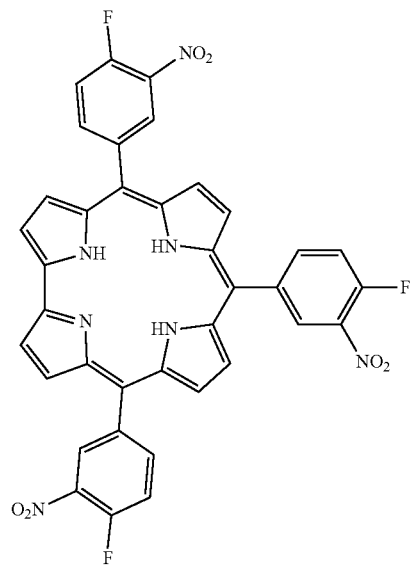
(C)
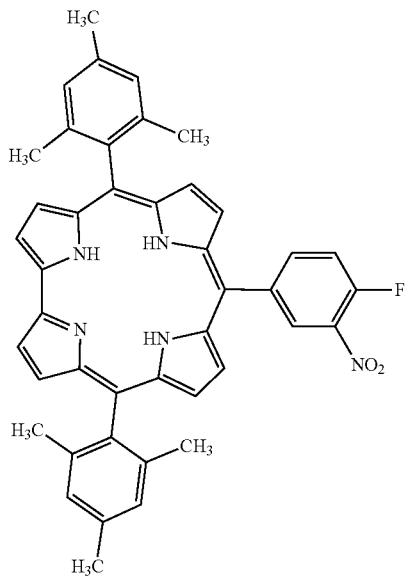
(D)
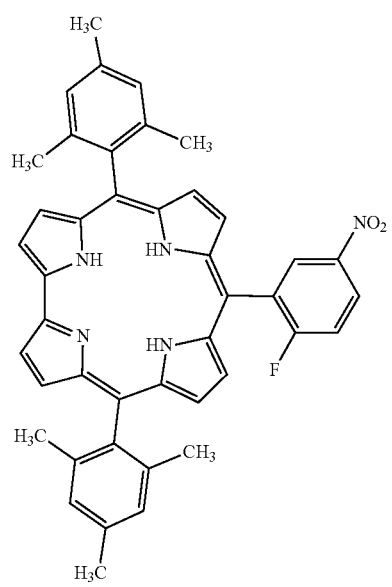
(E)
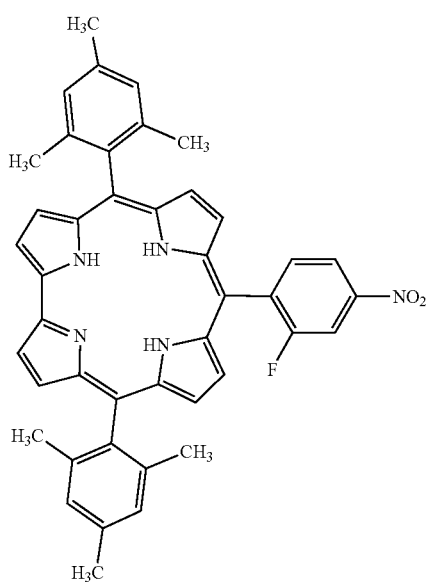
(F)

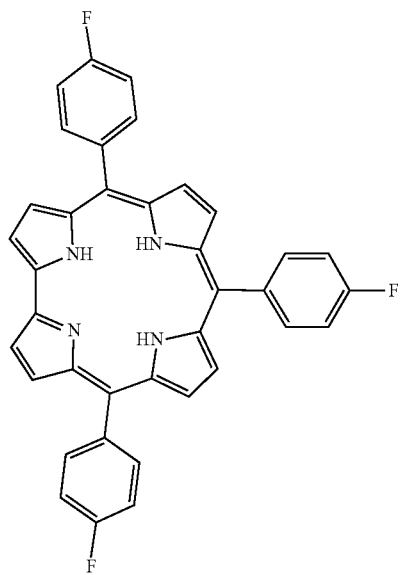 (G)
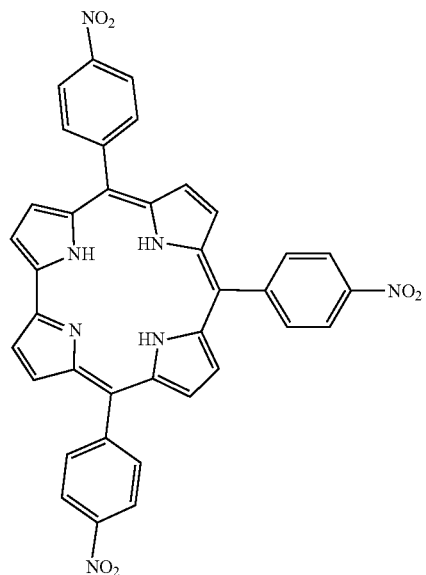 (H)
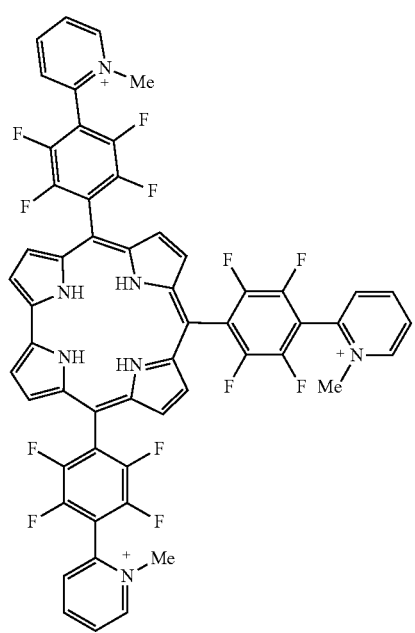 (I)
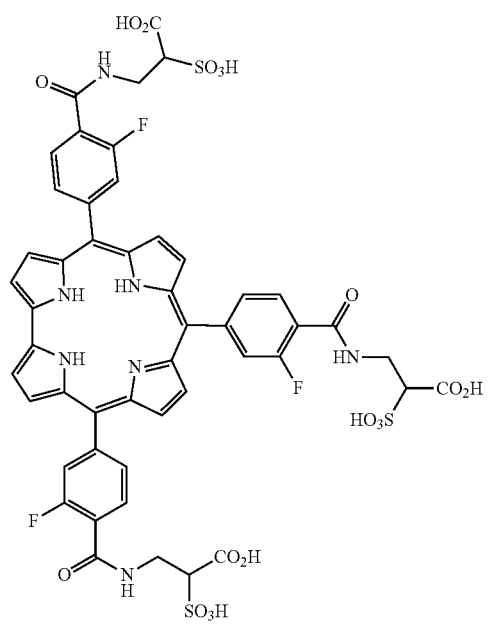 (J)

-continued
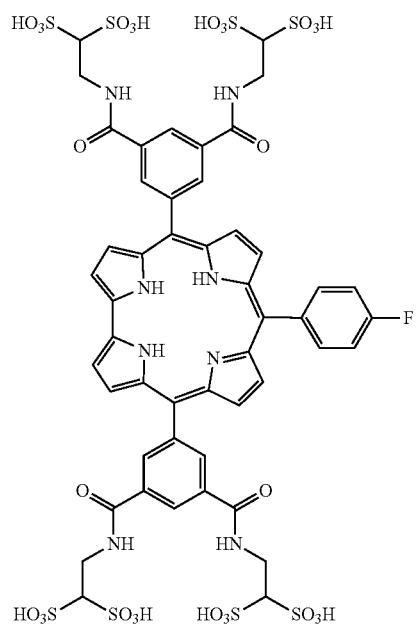
(K)
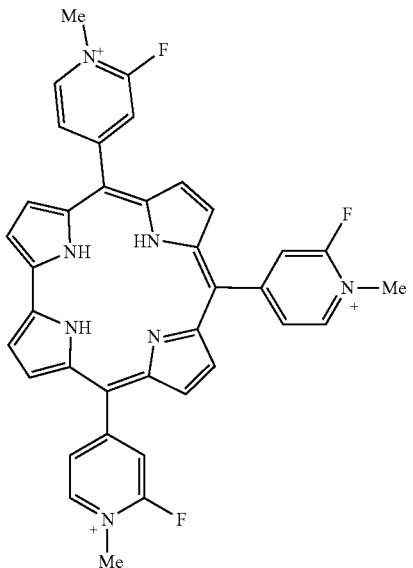
(L)
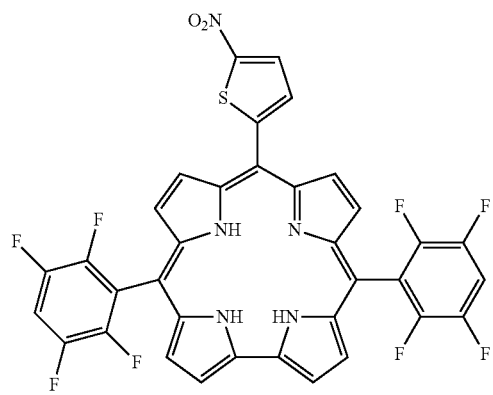
(M)
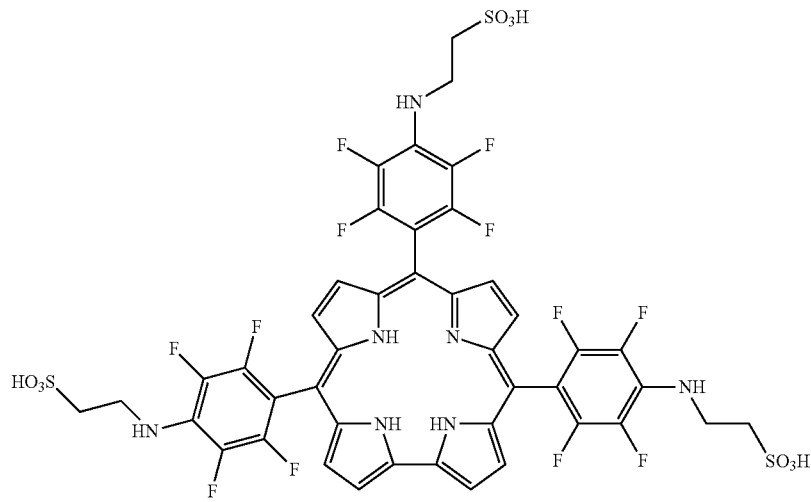
(N)
or a pharmaceutically acceptable salt thereof, or an optical isomer thereof.
14. The method of claim 5, wherein the corrole is chosen from following compounds

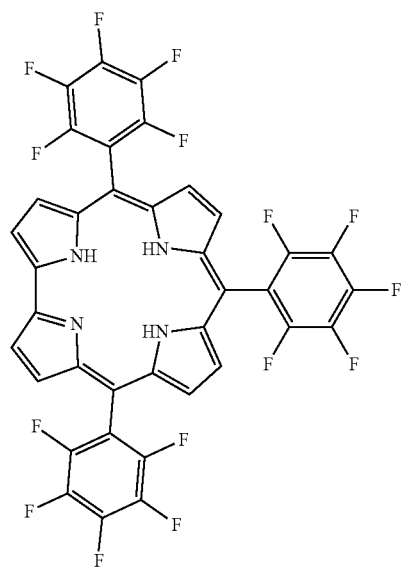
(A)
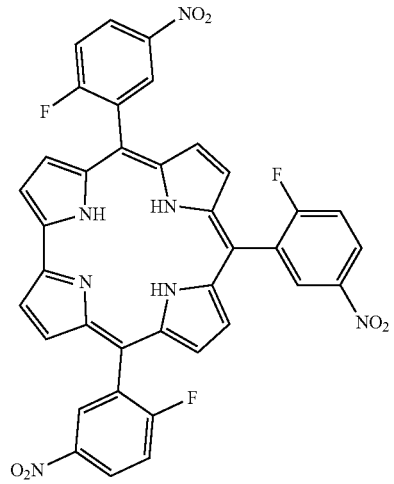
(B)
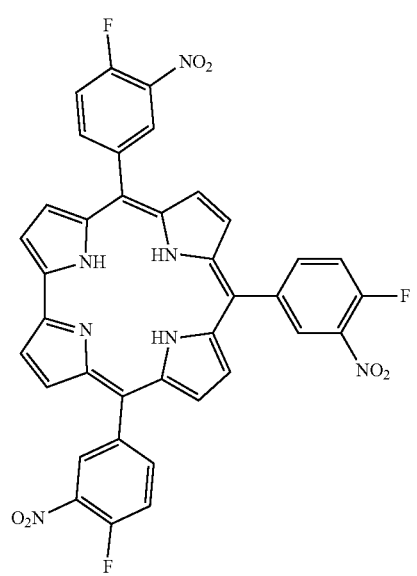
(C)
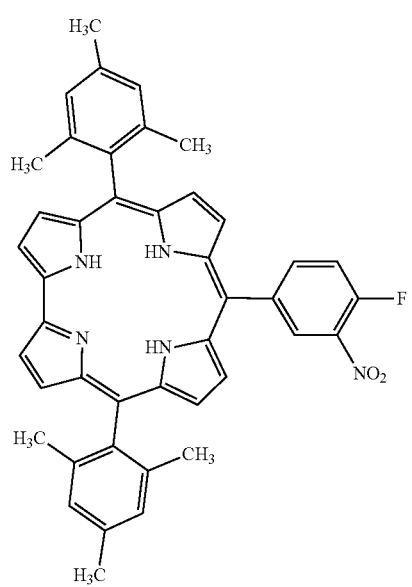
(D)

-continued
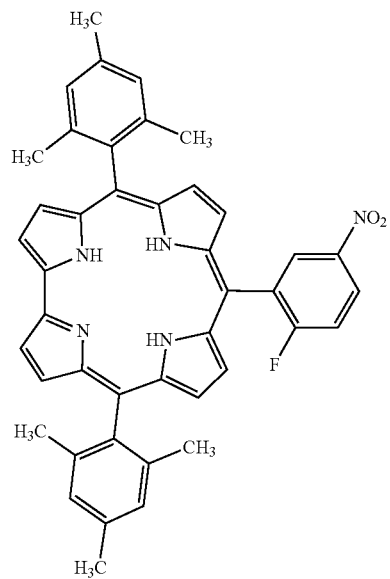
(E)
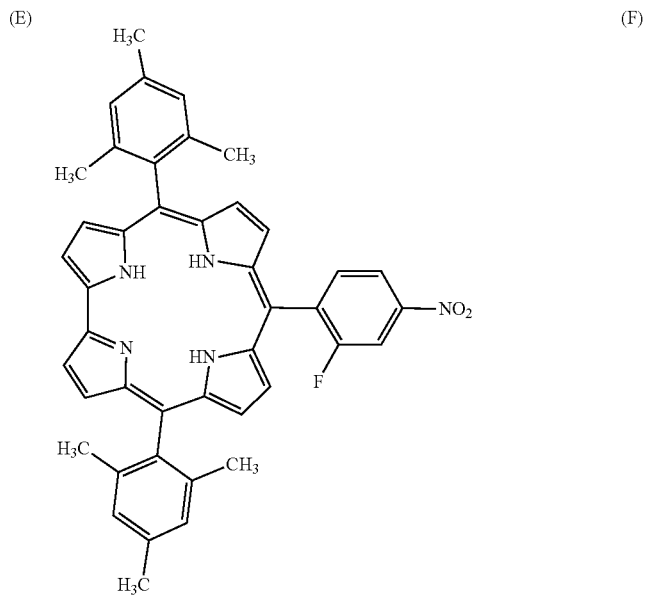
(F)
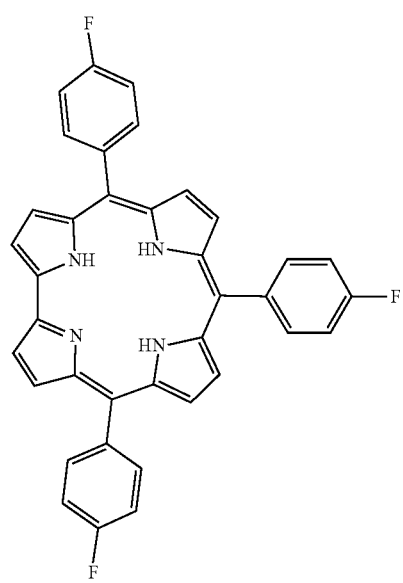
(G)
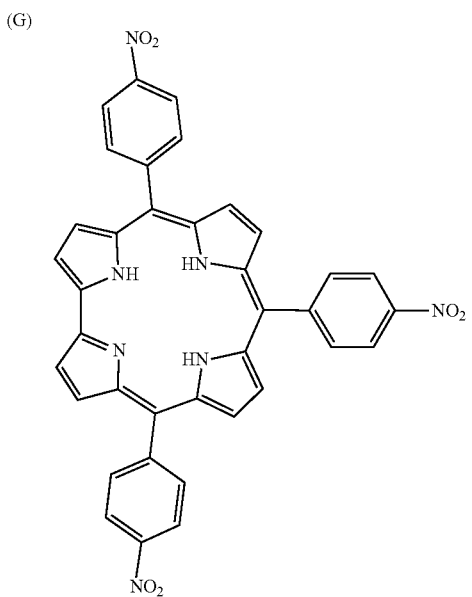
(H)

-continued
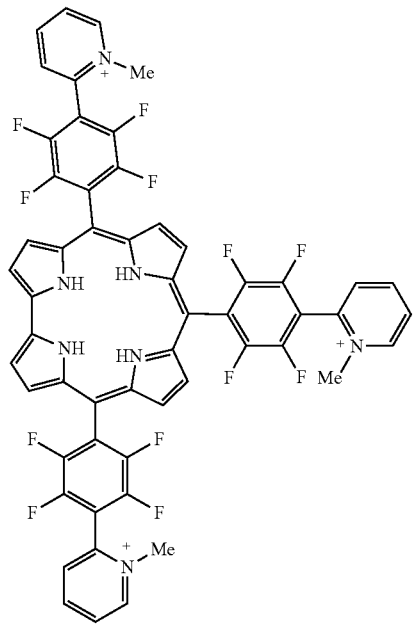
(I)
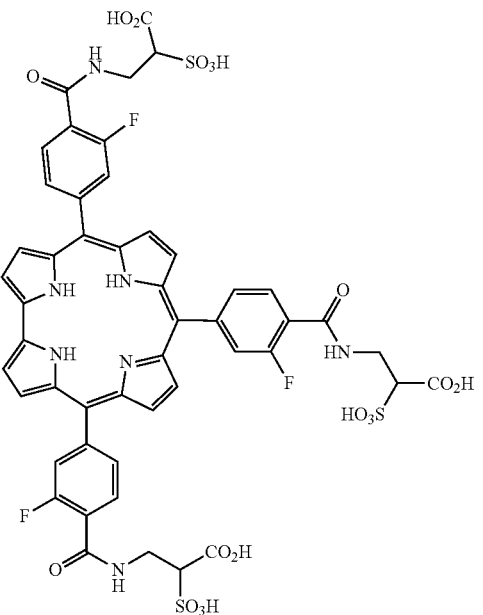
(J)
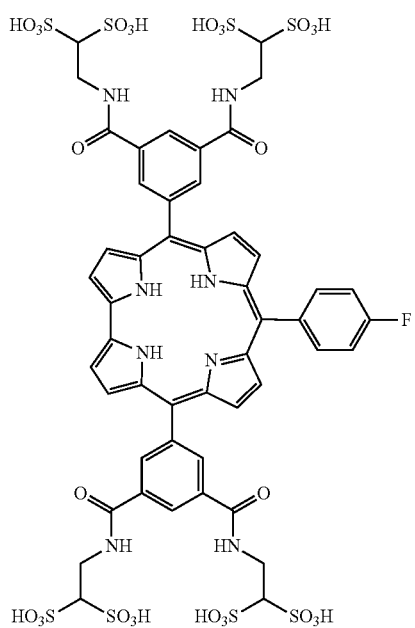
(K)
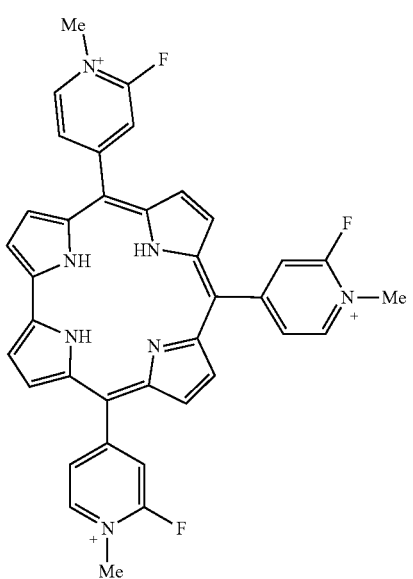
(L)
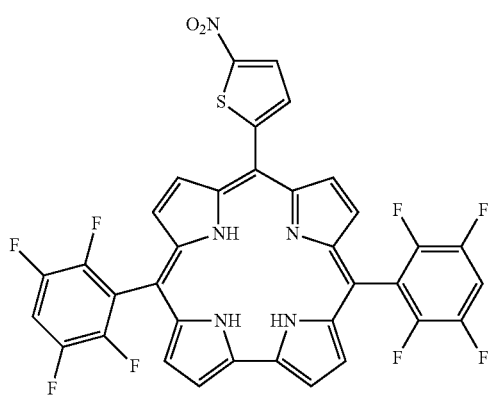
(M)

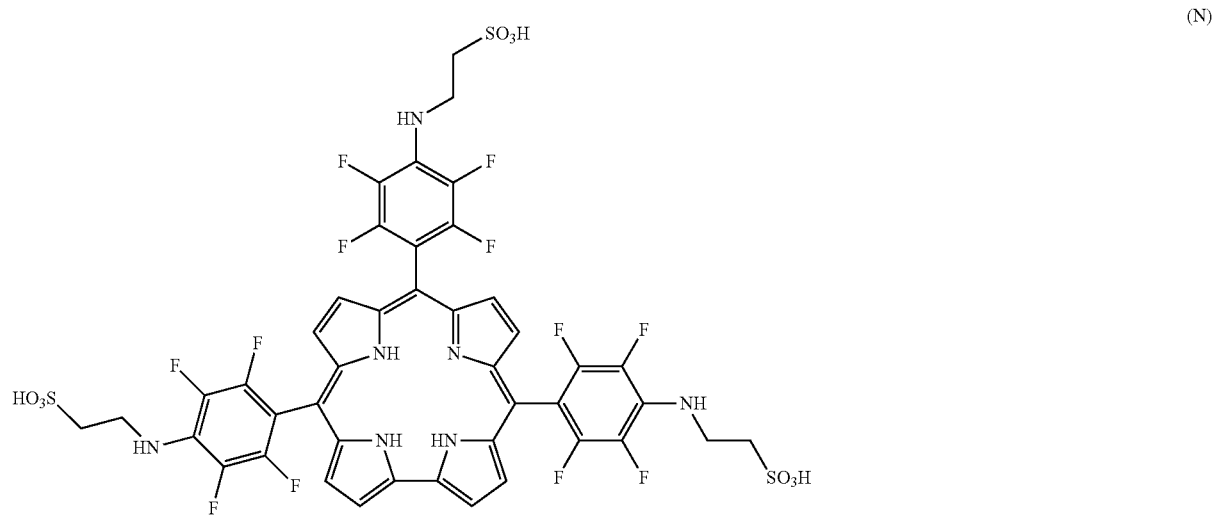
(N)
or a pharmaceutically acceptable salt thereof, or an optical isomer thereof.
15. The method of claim 6, wherein the corrole is chosen from following compounds
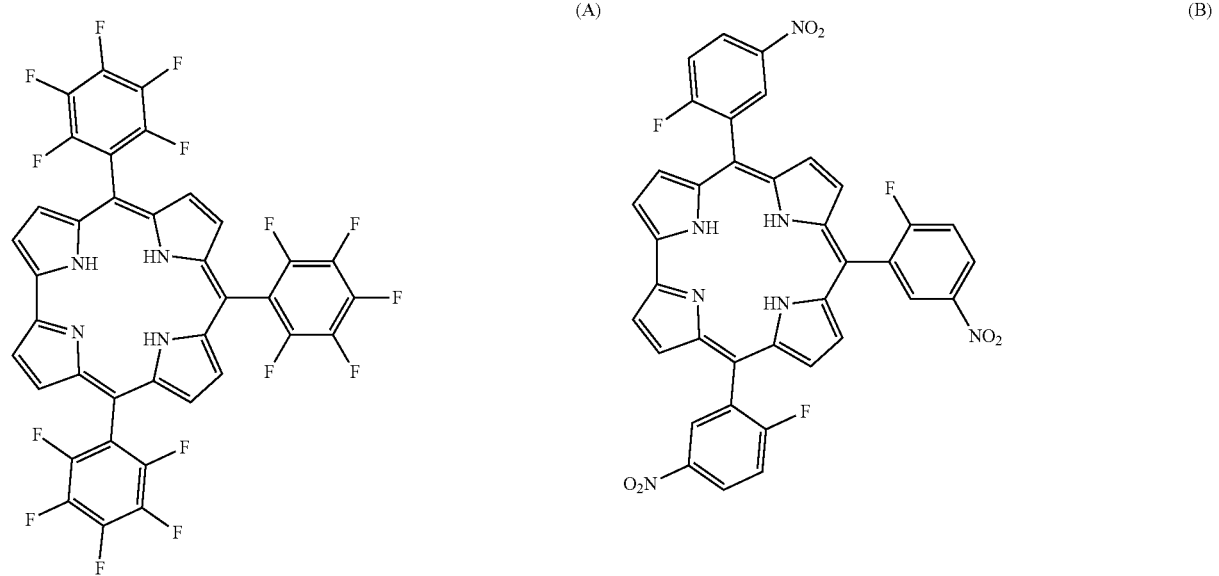
(A)
(B)

-continued
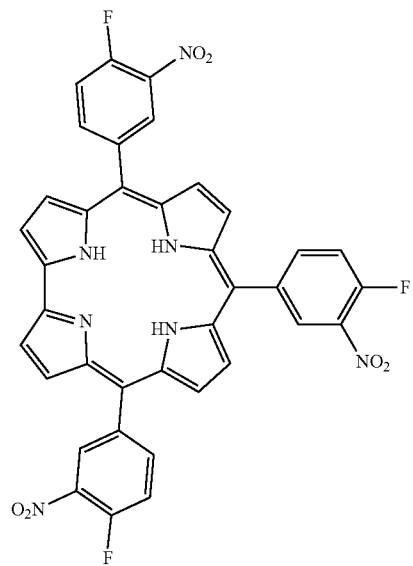
(C)
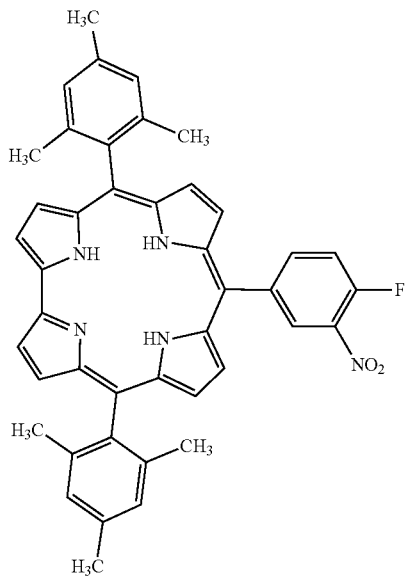
(D)
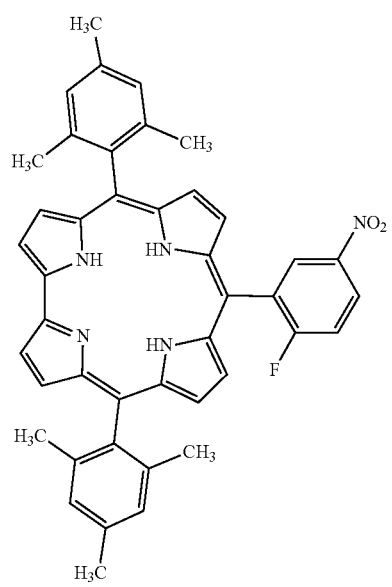
(E)
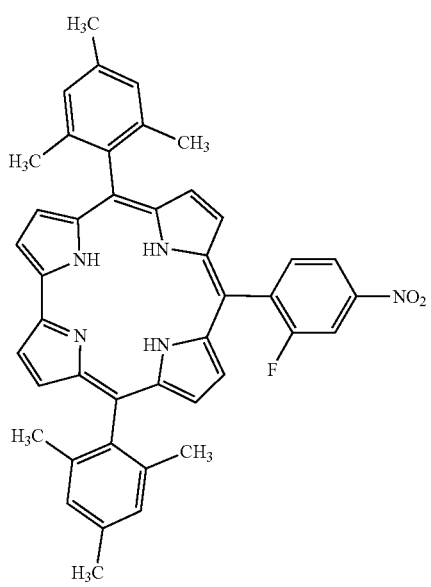
(F)

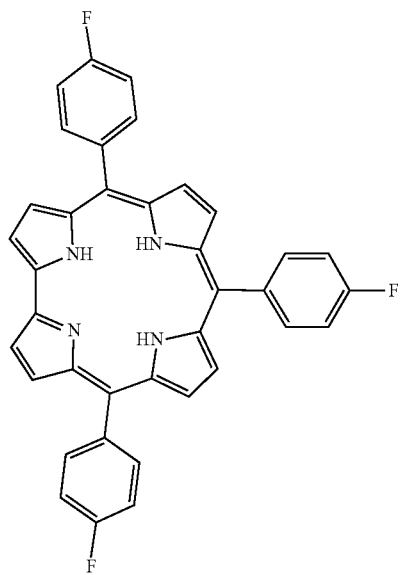
(G)
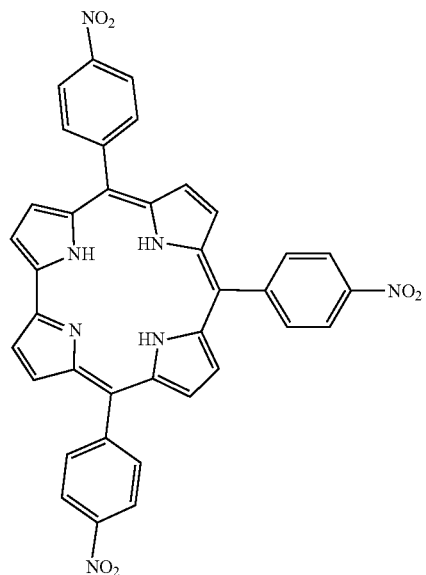
(H)
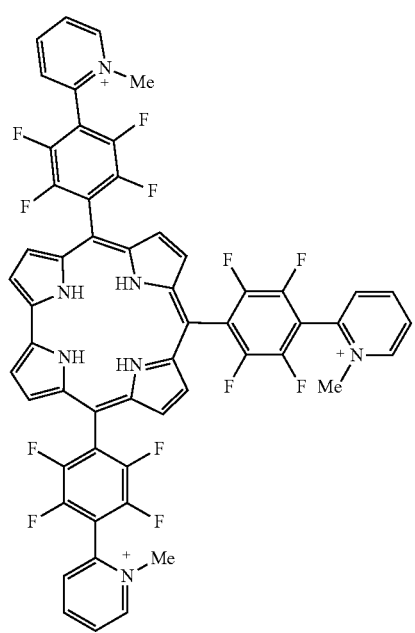
(I)
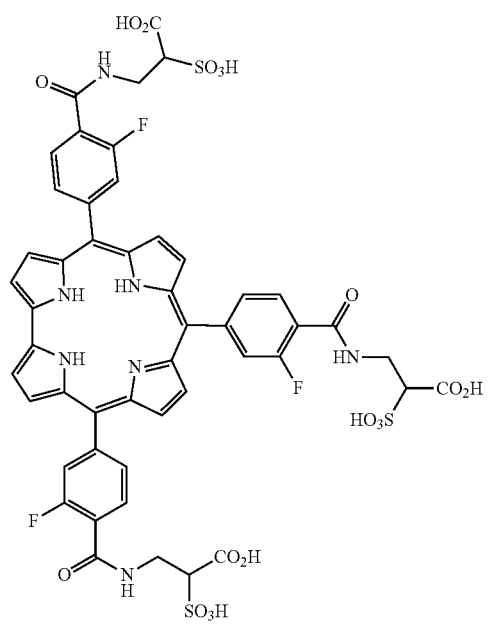
(J)

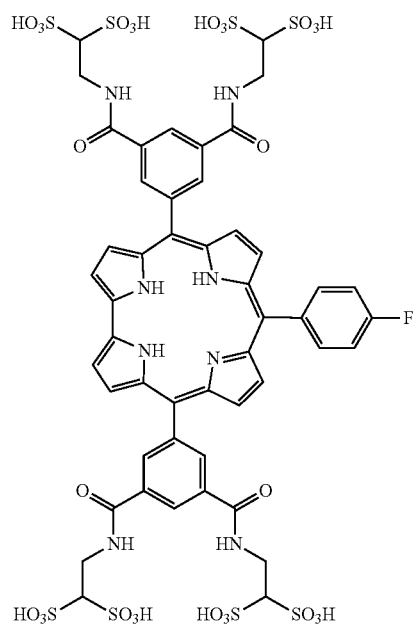
(K)
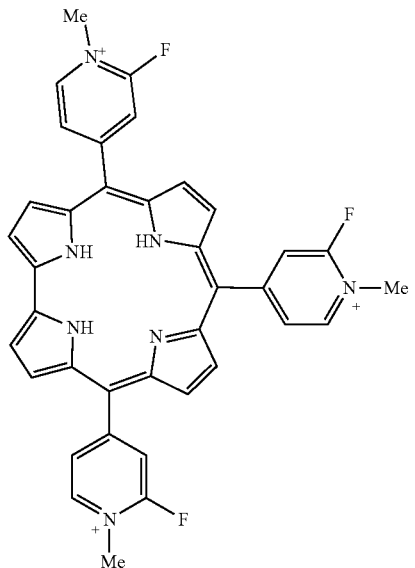
(L)
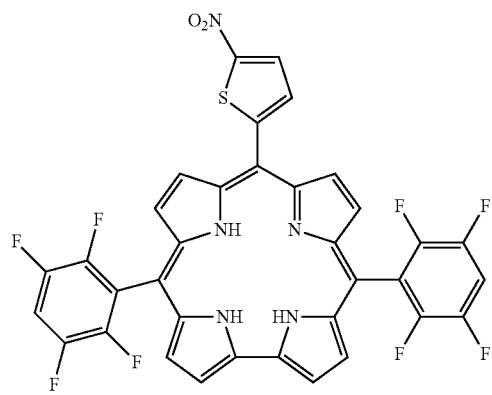
(M)
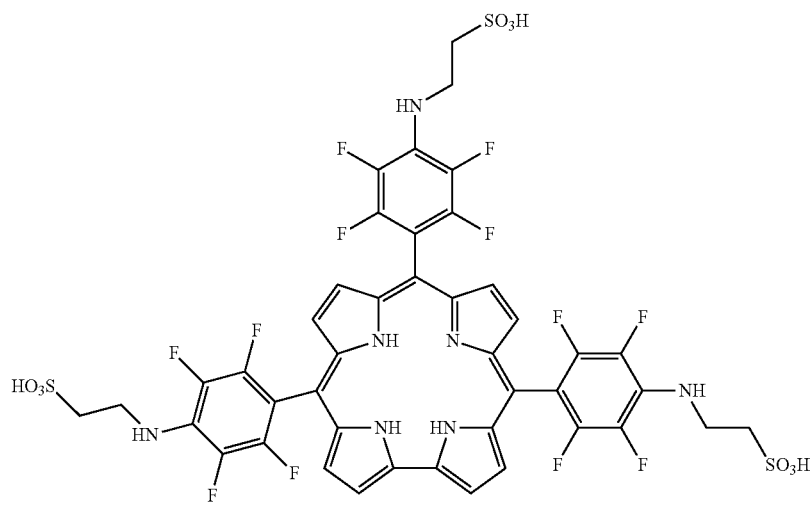
(N)
or a pharmaceutically acceptable salt thereof, or an optical isomer thereof.
* * * * *